United States Patent
Nii et al.

(10) Patent No.: US 11,229,615 B2
(45) Date of Patent: Jan. 25, 2022

(54) METHOD OF TREATING AND/OR PREVENTING INFLAMMATION BY ADMINISTERING OLANEXIDINE

(71) Applicant: OTSUKA PHARMACEUTICAL FACTORY, INC., Tokushima (JP)

(72) Inventors: Takuya Nii, Tokushima (JP); Akifumi Hagi, Tokushima (JP); Yoshie Tsubotani, Tokushima (JP)

(73) Assignee: OTSUKA PHARMACEUTICAL FACTORY, INC., Tokushima (JP)

( * ) Notice: Subject to any disclaimer, the term of this patent is extended or adjusted under 35 U.S.C. 154(b) by 36 days.

(21) Appl. No.: 16/605,363

(22) PCT Filed: Apr. 10, 2018

(86) PCT No.: PCT/JP2018/014999
§ 371 (c)(1),
(2) Date: Oct. 15, 2019

(87) PCT Pub. No.: WO2018/193904
PCT Pub. Date: Oct. 25, 2018

(65) Prior Publication Data
US 2021/0121417 A1   Apr. 29, 2021

(30) Foreign Application Priority Data
Apr. 19, 2017  (JP) .............................. JP2017-082793

(51) Int. Cl.
*A61K 31/155*   (2006.01)
*A61P 29/00*    (2006.01)
(Continued)

(52) U.S. Cl.
CPC .............. *A61K 31/155* (2013.01); *A61K 9/08* (2013.01); *A61K 47/34* (2013.01); *A61P 29/00* (2018.01)

(58) Field of Classification Search
CPC ........ A61K 31/155; A61K 9/00; A61K 47/34; A61K 47/10; A61P 29/00; A61P 1/02; A61P 11/00; A61P 43/00
See application file for complete search history.

(56) References Cited

U.S. PATENT DOCUMENTS

2003/0124190 A1   7/2003 Williams et al.
2006/0115520 A1   6/2006 Vanek et al.
(Continued)

FOREIGN PATENT DOCUMENTS

CN   102715184       4/2016
EP   0507317 A2      4/1992
(Continued)

OTHER PUBLICATIONS

Nii et al, Anti-inflammatory effects of olanexidine gluconate on oral epithelial cells, • Medicine • BMC Oral Health (Year: 2019).*
(Continued)

*Primary Examiner* — Carlos A Azpuru
(74) *Attorney, Agent, or Firm* — Greenblum & Bernstein, P.L.C.

(57) ABSTRACT

An object of the present invention is to provide a composition that can be used as a novel anti-inflammatory agent. An inflammation such as stomatitis, oral mucositis, gingivitis, or pneumonia can be ameliorated and/or prevented by using a composition comprising olanexidine or a pharmacologically acceptable salt thereof. The composition of the present invention preferably further comprises a poloxamer which is a block copolymer consisting of a chain of polyoxypropylene (POP) and two chains of polyoxyethylene (POE) flanking the POP.

9 Claims, 17 Drawing Sheets

(51) Int. Cl.
  *A61K 9/08*   (2006.01)
  *A61K 47/34*  (2017.01)

(56) References Cited

U.S. PATENT DOCUMENTS

2006/0189500 A1   8/2006   Miyata et al.
2007/0053942 A1   3/2007   Nishibayashi et al.
2007/0231051 A1   10/2007  Flores et al.

FOREIGN PATENT DOCUMENTS

| EP | 0507317 A2 | 10/1992 |
| JP | 2004-352635 | 12/2004 |
| JP | 2005-22995 | 1/2005 |
| JP | 2005-289959 | 10/2005 |
| JP | 2005-343964 | 12/2005 |
| JP | 2009-526624 | 7/2009 |
| JP | 2017-78046 | 4/2017 |
| RU | 2404826 | 11/2010 |
| WO | 2004/105745 | 12/2004 |
| WO | 2015193337 | 12/2015 |

OTHER PUBLICATIONS

Nii et al, Antiinflammatory Effects of Olanexidine Gluconate On Oral Epitheialial Cells, Medicine BMC Oral Health. (Year: 2019).*
Hagi A. et al., "Bactericidal Effects and Mechanism of Action of Olanexidine Gluconate, a New Antiseptic," *Antimicrobial Agents and chemotherapy*, Aug. 2015, V.59 No. 8 pp. 4551-4559.
"Evaluation and Licensing Division, Pharmaceutical and Food Safety Bureau, Ministry o Health, Labour and Welfare, [Brand name] Olanedine Antiseptic Solution 1.5%; Olanedine Solution 1.5% Antiseptic Applicator 10mL; Olanedine Solution 1.5% Antiseptic Applicator 25mL, Report on the Deliberation Results", The Pharmaceuticals and Medical Devices Agency, Jun. 22, 2015, pp. 1-68, p. 33 lines 1-17, table 20.
Akifumi Hagi et al., "Bactericidal Effects and Mechanism of Action of Olanexidine Gluconate, a New Antiseptic", Antimicrobial Agents and Chemotherapy, vol. 59, No. 8, Aug. 2015, pp. 4551-4559.
International Search Report issued in International Patent Application No. PCT/JP2018/014999, dated Jun. 12, 2018 with English Translation.

* cited by examiner

[Fig. 1]
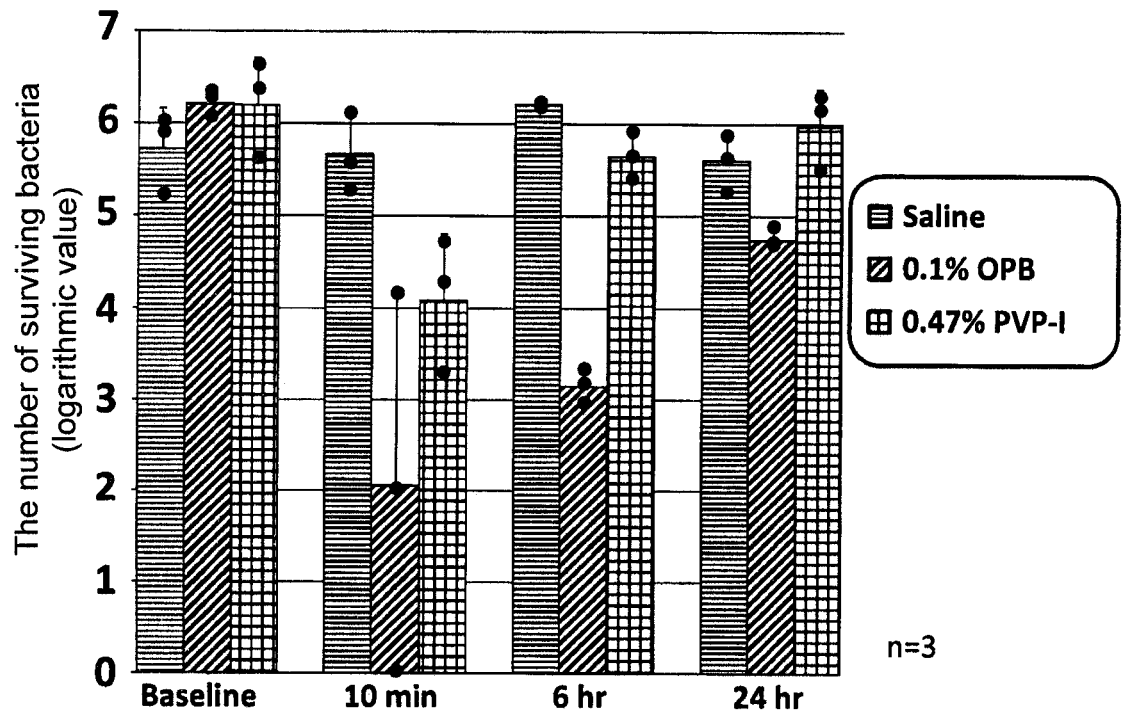
[Fig. 2]
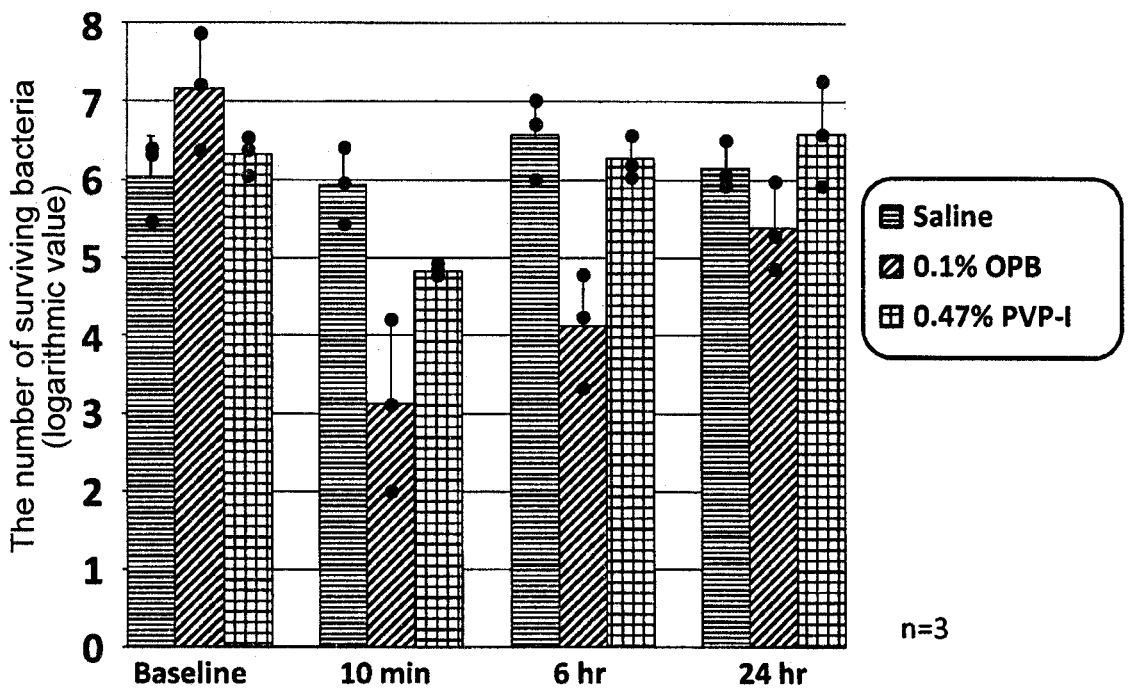

[Fig 3]
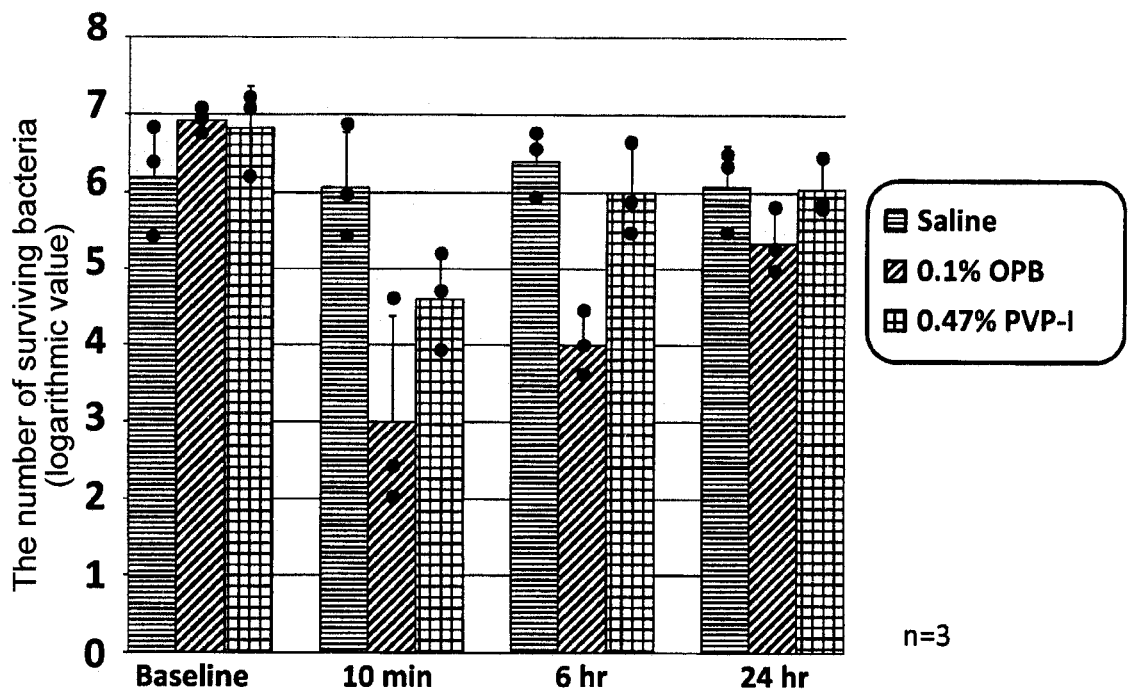
[Fig. 4]
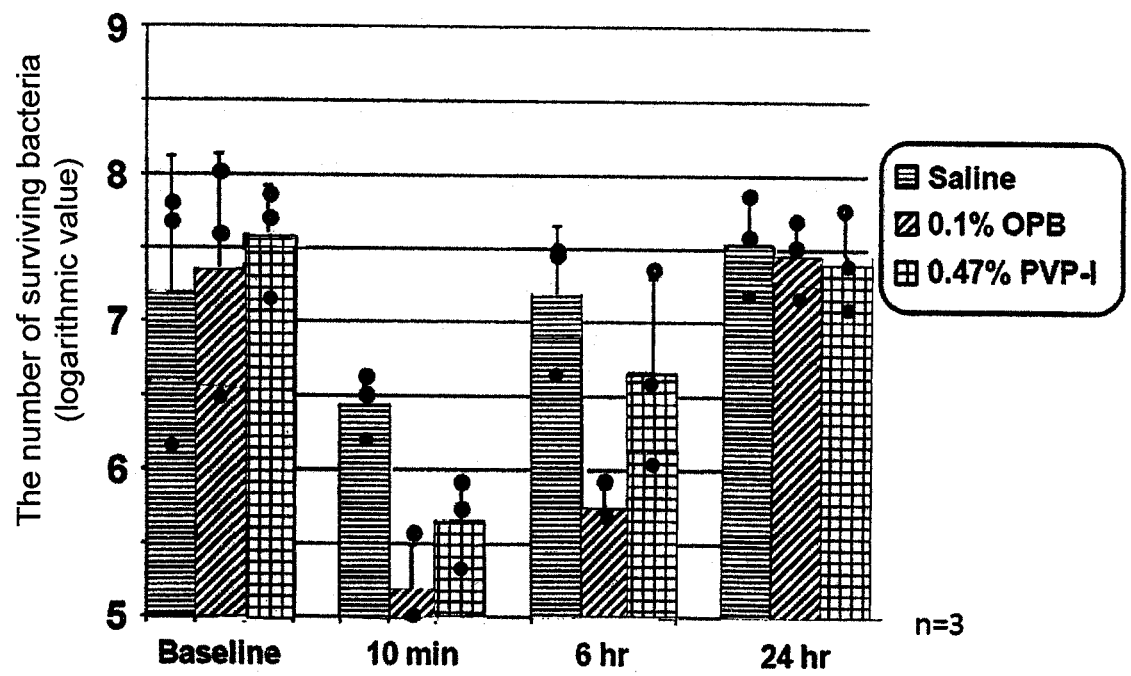

[Fig. 5]
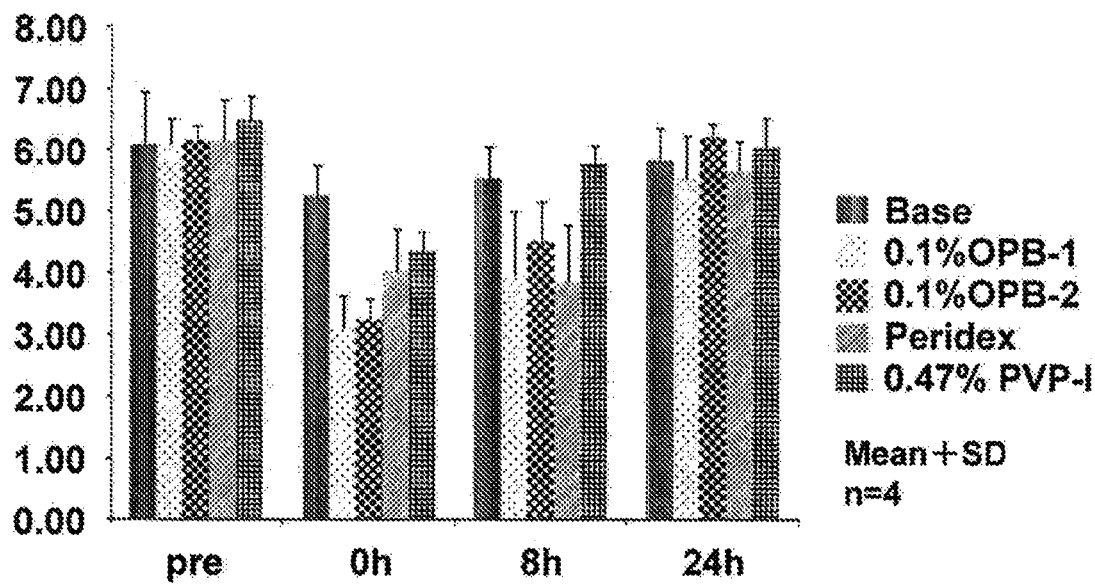
[Fig. 6]
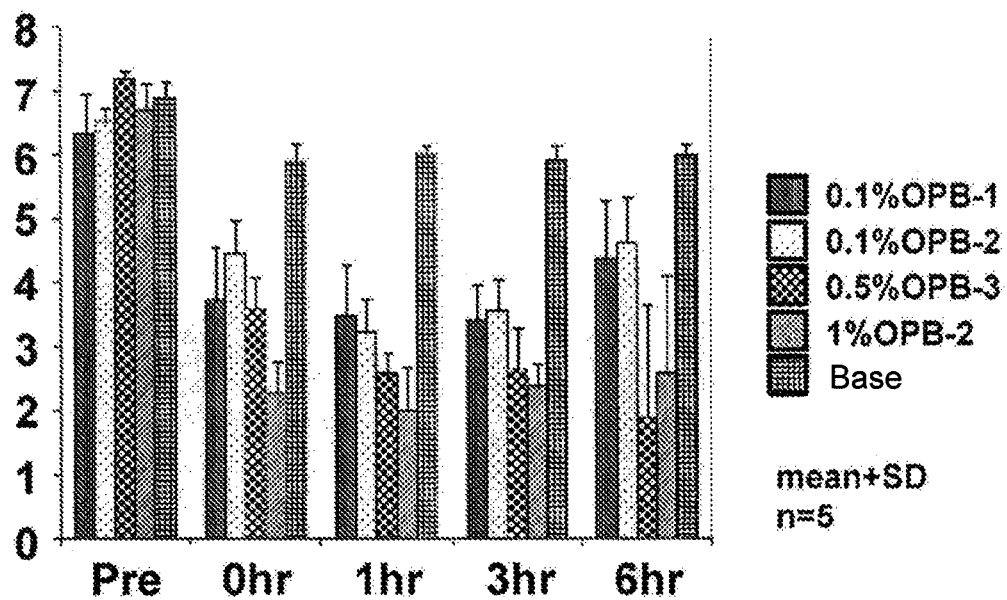

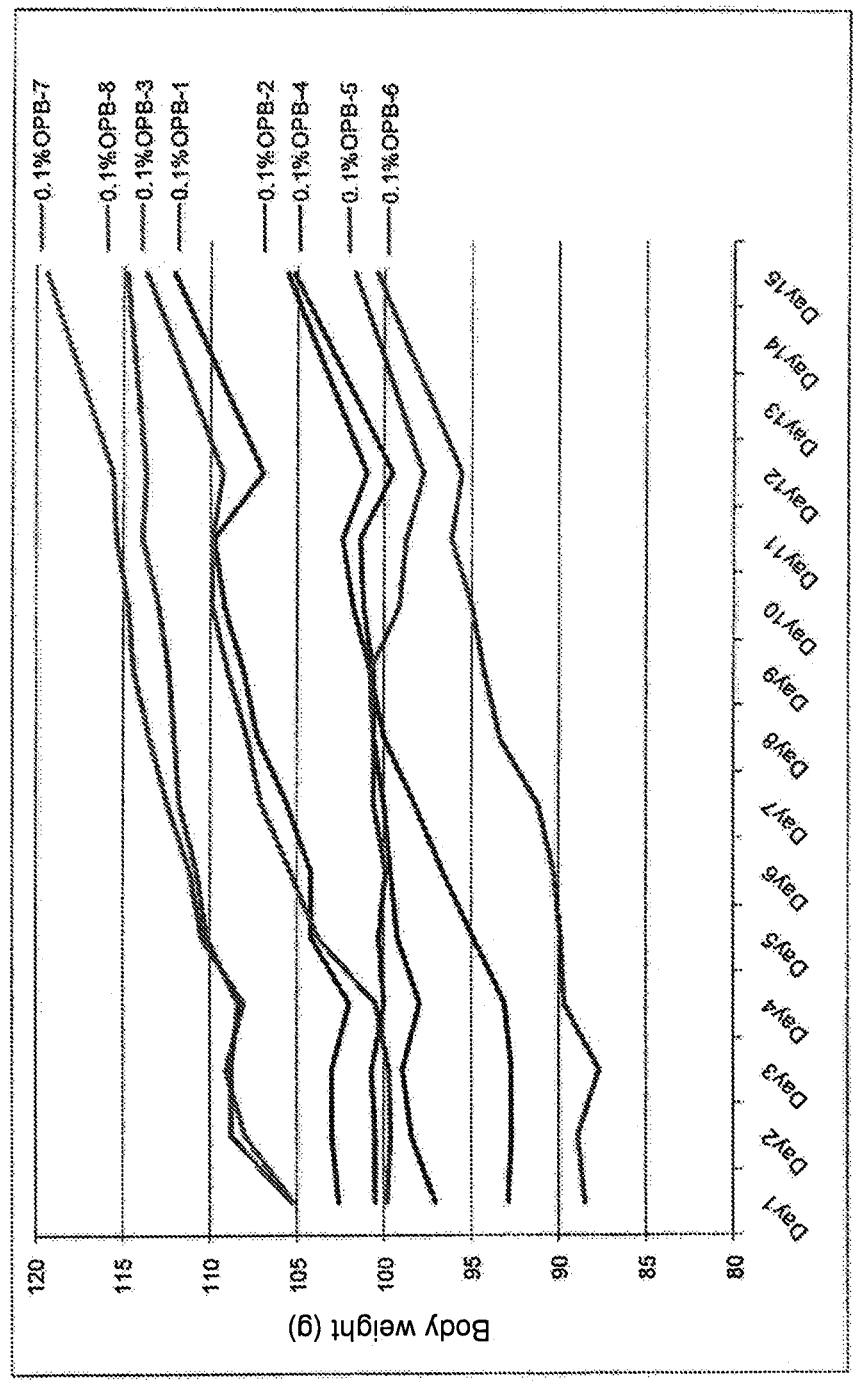
[Fig. 7]

[Fig. 8]

[Fig. 9A]
Photo 1 0.1%OPB-1 group
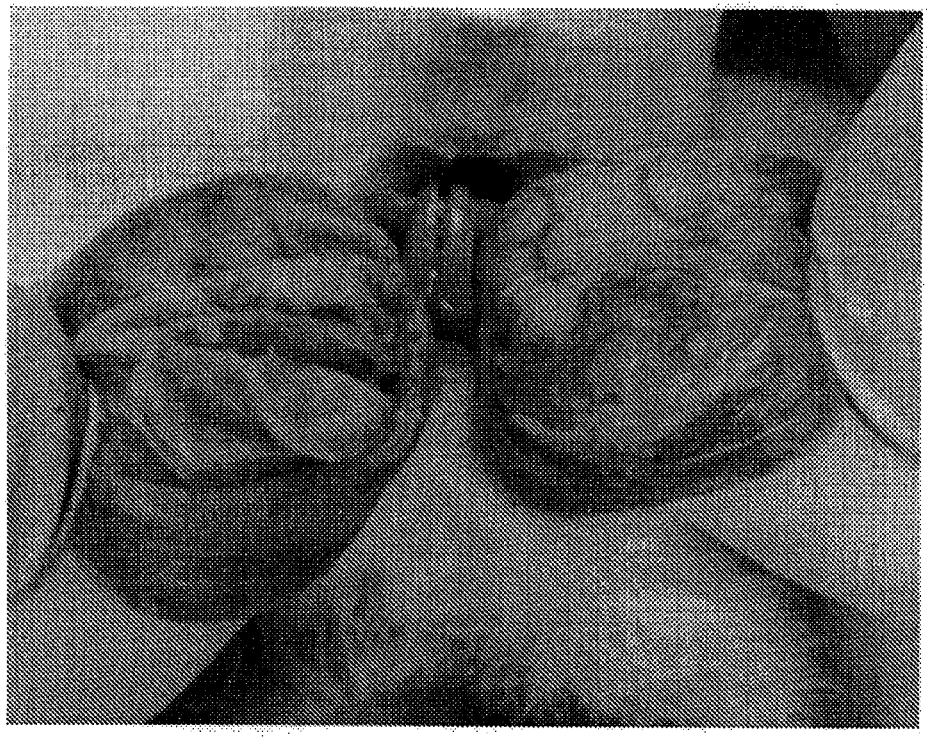
Photo 2 0.1%OPB-2 group

[Fig. 9B]
Photo 3 0.1%OPB-3 group
Photo 4 0.1%OPB-4 group
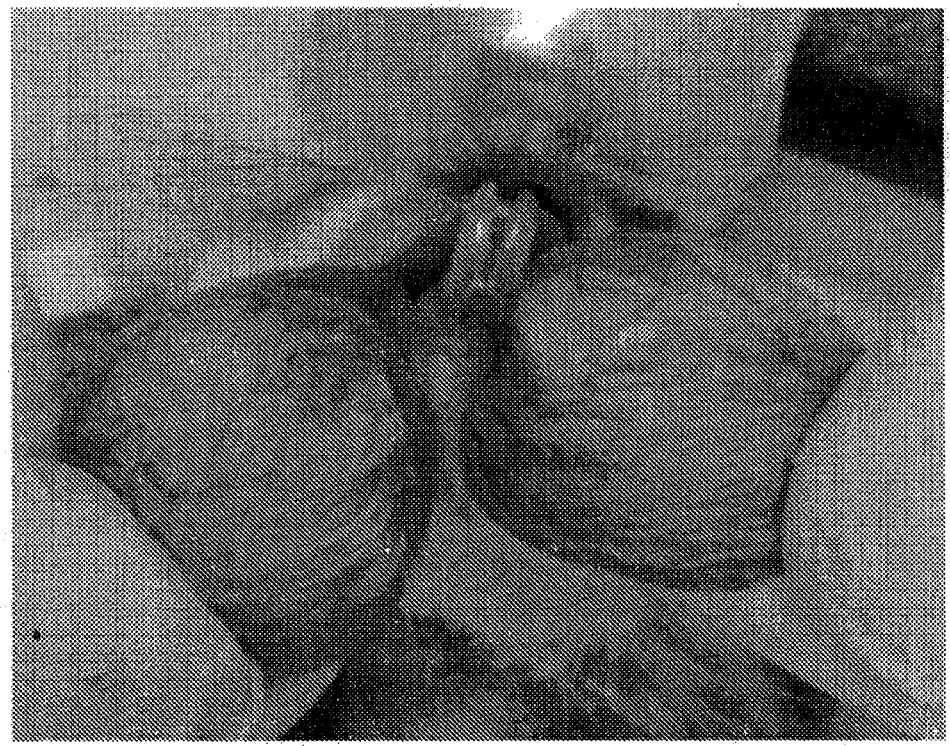

[Fig. 9C]
Photo 5 0.1%OPB-5 group
Photo 6 0.1%OPB-6 group

[Fig. 9D]
Photo 7 0.1%OPB-7 group
Photo 8 0.1%OPB-8 group

[Fig. 10]

| Organ: | Group | 0.1% OPB-1 | | | 0.1% OPB-2 | | | 0.1% OPB-3 | | | 0.1% OPB-4 | | | 0.1% OPB-5 | | |
|---|---|---|---|---|---|---|---|---|---|---|---|---|---|---|---|---|
| Histopathological manifestation | Animal No. | 1 | 2 | 3 | 4 | 5 | 6 | 7 | 8 | 9 | 10 | 11 | 12 | 13 | 14 | 15 |
| | Sample No. | 2 | 4 | 6 | 8 | 10 | 12 | 14 | 16 | 18 | 20 | 22 | 24 | 26 | 28 | 30 |
| Right cheek pouch, oral mucosa | | | | | | | | | | | | | | | | |
| Epithelium (cell degeneration, metaplasia, or erosion) | | 0 | 0 | 1 | 0 | 1 | 1 | 0 | 0 | 0 | 0 | 1 | 0 | 0 | 1 | 1 |
| Leukocyte infiltration | | 2 | 1 | 2 | 1 | 3 | 1 | 0 | 0 | 0 | 0 | 2 | 0 | 0 | 1 | 1 |
| Vascular congestion | | 0 | 0 | 0 | 0 | 0 | 0 | 0 | 0 | 0 | 0 | 0 | 0 | 0 | 0 | 0 |
| Edema | | 0 | 0 | 0 | 0 | 0 | 0 | 0 | 0 | 0 | 0 | 0 | 0 | 0 | 0 | 0 |
| Inflammation index | | 2 | 1 | 3 | 1 | 4 | 2 | 0 | 0 | 0 | 0 | 3 | 0 | 0 | 2 | 2 |
| Average grade | | 2 | | | 2 | | | 0 | | | 1 | | | 1 | | |
| Other manifestations | | | | | | | | | | | | | | | | |
| Intercellular edema | | − | − | ± | − | ± | − | − | − | − | − | − | − | − | − | − |
| Increased keratosis | | + | + | + | + | +† | + | − | − | − | ± | ± | ± | ± | ± | ± |

Grade in other manifestations −: within normal limited, ±: very slight, +: slight, 2+: moderate, 3+:severe
†: parakeratotic

| Organ: | Group | 0.1% OPB-6 | | | 0.1% OPB-7 | | | 0.1% OPB-8 | | |
|---|---|---|---|---|---|---|---|---|---|---|
| | Animal No. | 16 | 17 | 18 | 19 | 20 | 21 | 22 | 23 | 24 |
| Histopathological manifestation | Sample No. | 32 | 34 | 36 | 38 | 40 | 42 | 44 | 46 | 48 |
| Right cheek pouch, oral mucosa | | | | | | | | | | |
| Epithelium (cell degeneration, metaplasia, or erosion) | | 1 | 1 | 1 | 1 | 1 | 1 | 1 | 1 | 1 |
| Leukocyte infiltration | | 1 | 1 | 2 | 1 | 1 | 2 | 3 | 2 | 2 |
| Vascular congestion | | 0 | 0 | 0 | 0 | 0 | 0 | 0 | 0 | 0 |
| Edema | | 0 | 0 | 0 | 0 | 0 | 0 | 0 | 0 | 0 |
| Inflammation index | | 2 | 2 | 3 | 2 | 2 | 3 | 4 | 3 | 3 |
| Average grade | | 2 | | | 2 | | | 3 | | |
| Other manifestations | | | | | | | | | | |
| Intercellular edema | | − | − | − | − | − | − | ± | − | − |
| Increased keratosis | | + | + | + | + | +† | + | + | + | + |

Grade in other manifestations −: within normal limited, ±: very slight, +: slight, 2+: moderate, 3+:severe
†: parakeratotic

| Organ: | Group | Control(DW) | | | | | | | | | | | | | | | | | | | | | | | |
|---|---|---|---|---|---|---|---|---|---|---|---|---|---|---|---|---|---|---|---|---|---|---|---|---|---|
| Histopathological manifestation | Animal No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| | Sample No. | 1 | 3 | 5 | 7 | 9 | 11 | 13 | 15 | 17 | 19 | 21 | 23 | 25 | 27 | 29 | 31 | 33 | 35 | 37 | 39 | 41 | 43 | 45 | 47 |
| Right cheek pouch, oral mucosa | | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Epithelium (cell degeneration, metaplasia, or erosion) | | 0 | 0 | 0 | 0 | 0 | 0 | 0 | 0 | 0 | 0 | 0 | 0 | 2 | 1 | 0 | 0 | 0 | 0 | 0 | 0 | 0 | 0 | 0 | 2 |
| Leukocyte infiltration | | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Vascular congestion | | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Edema | | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Inflammation index | | 0 | 0 | 0 | 0 | 0 | 0 | 0 | 0 | 0 | 0 | 0 | 0 | 2 | 1 | 0 | 0 | 0 | 0 | 0 | 0 | 0 | 0 | 0 | 2 |
| Average grade | | | | | | | | | | | | | 0 | | | | | | | | | | | | |
| Other manifestations | | | | | | | | | | | | | | | | | | | | | | | | | |
| Intercellular edema | | − | − | − | − | − | − | − | − | − | − | − | − | − | − | − | − | − | − | − | − | − | − | − | − |
| Increased keratosis | | − | − | − | − | − | − | − | − | − | − | − | − | − | − | − | − | − | − | − | − | − | − | − | − |

Grade in other manifestations −: within normal limited, ±: very slight, +: slight, 2+: moderate, 3+:severe

| Organ: Histopathological manifestation | Group | 0.1% OPB-1 | | | 0.1% OPB-2 | | | 0.1% OPB-3 | | | 0.1% OPB-4 | | | 0.3% OPB-1 | | | 0.3% OPB-2 | | |
|---|---|---|---|---|---|---|---|---|---|---|---|---|---|---|---|---|---|---|---|
| | Animal No. | 1 | 2 | 3 | 4 | 5 | 6 | 7 | 8 | 9 | 10 | 11 | 12 | 19 | 20 | 21 | 22 | 23 | 24 |
| | Sample No. | 1L | 2L | 3L | 4L | 5L | 6L | 7L | 8L | 9L | 10L | 11L | 12L | 19L | 20L | 21L | 22L | 23L | 24L |
| Right cheek pouch, oral mucosa | | | | | | | | | | | | | | | | | | | | |
| Epithelium (cell degeneration, metaplasia, or erosion) | | 0 | 0 | 0 | 0 | 0 | 0 | 0 | 0 | 0 | 0 | 0 | 0 | 1 | 1 | 1 | 1 | 1 | 0 |
| Leukocyte infiltration | | 0 | 0 | 0 | 0 | 0 | 0 | 0 | 0 | 0 | 0 | 0 | 0 | 1 | 1 | 1 | 0 | 0 | 0 |
| Vascular congestion | | 0 | 0 | 0 | 0 | 0 | 0 | 0 | 0 | 0 | 0 | 0 | 0 | 0 | 0 | 0 | 0 | 0 | 0 |
| Edema | | 0 | 0 | 0 | 0 | 0 | 0 | 0 | 0 | 0 | 0 | 0 | 0 | 0 | 0 | 0 | 0 | 0 | 0 |
| Inflammation index | | 0 | 0 | 0 | 0 | 0 | 0 | 0 | 0 | 0 | 0 | 0 | 0 | 2 | 2 | 2 | 1 | 1 | 0 |
| Average grade | | 0 | | | 0 | | | 0 | | | 0 | | | 2 | | | 1 | | |
| Other manifestations | | | | | | | | | | | | | | | | | | | | |
| Intercellular edema | | ± | − | − | ± | − | ± | − | + | − | − | − | ± | + | + | 2+ | + | + | + |
| Increased keratosis | | − | − | − | − | − | − | − | − | − | − | − | − | − | ± | ± | − | − | − |
| Intraepidermal microabscess | | − | − | − | − | − | − | − | − | − | − | − | − | − | − | − | − | − | − |

Grade in other manifestations −: within normal limited, ±: very slight, +: slight, 2+: moderate, 3+: severe

| Organ: Histopathological manifestation | Group | 0.5% OPB-1 | | | 0.5% OPB-2 | | | 0.5% OPB-3 | | | 0.5% OPB-4 | | |
|---|---|---|---|---|---|---|---|---|---|---|---|---|---|
| | Animal No. | 31 | 32 | 33 | 34 | 35 | 36 | 37 | 38 | 39 | 40 | 41 | 42 |
| | Sample No. | 31L | 32L | 33L | 34L | 35L | 36L | 37L | 38L | 39L | 40L | 41L | 42L |
| Right cheek pouch, oral mucosa | | | | | | | | | | | | | |
| Epithelium (cell degeneration, metaplasia, or erosion) | | 1 | 1 | 1 | 1 | 1 | 1 | 1 | 1 | 1 | 0 | 1 | 1 |
| Leukocyte infiltration | | 2 | 1 | 2 | 0 | 0 | 0 | 1 | 1 | 1 | 0 | 1 | 1 |
| Vascular congestion | | 0 | 0 | 0 | 0 | 0 | 0 | 0 | 0 | 0 | 0 | 0 | 0 |
| Edema | | 0 | 0 | 0 | 0 | 0 | 0 | 0 | 0 | 0 | 0 | 0 | 0 |
| Inflammation index | | 3 | 2 | 3 | 1 | 1 | 1 | 2 | 2 | 2 | 0 | 2 | 2 |
| Average grade | | 3 | | | 1 | | | 2 | | | 1 | | |
| Other manifestations | | | | | | | | | | | | | |
| Intercellular edema | | 2+ | 2+ | 2+ | 2+ | + | ± | 2+ | 2+ | 2+ | + | 2+ | 2+ |
| Increased keratosis | | ± | ± | ± | − | − | − | − | ± | ± | − | − | ± |
| Intraepidermal microabscess | | − | − | − | − | − | − | − | − | − | − | − | − |

Grade in other manifestations −: within normal limited, ±: very slight, +: slight, 2+: moderate, 3+: severe

| Organ: Histopathological manifestation | Group | Control | | | | | | | | | | | | | | | | | | | | | | | |
|---|---|---|---|---|---|---|---|---|---|---|---|---|---|---|---|---|---|---|---|---|---|---|---|---|---|
| | Animal No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| | Sample No. | 1R | 2R | 3R | 4R | 5R | 6R | 7R | 8R | 9R | 10R | 11R | 12R | 13R | 14R | 15R | 16R | 17R | 18R | 19R | 20R | 21R | 22R | 23R | 24R |
| Right cheek pouch, oral mucosa | | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Epithelium (cell degeneration, metaplasia, or erosion) | | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Leukocyte infiltration | | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Vascular congestion | | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Edema | | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Inflammation index | | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Average grade | | | | | | | | | | | | | | 0 | | | | | | | | | | | |
| Other manifestations | | | | | | | | | | | | | | | | | | | | | | | | | |
| Intercellular edema | | − | − | − | − | − | − | − | − | − | − | − | − | − | − | − | − | − | − | − | − | − | − | − | − |
| Increased keratosis | | − | − | − | − | − | − | − | − | − | − | − | − | − | − | − | − | − | − | − | − | − | − | − | − |
| Intraepidermal microabscess | | − | − | ± | − | − | ± | − | − | − | − | − | − | − | − | − | − | − | − | − | − | − | − | − | − |

Grade in other manifestations −: within normal limited, ±: very slight, +: slight, 2+: moderate, 3+: severe

| Organ: Histopathological manifestation | Group | Control | | | | | | | | | | | |
|---|---|---|---|---|---|---|---|---|---|---|---|---|---|
| | Animal No. | 31 | 32 | 33 | 34 | 35 | 36 | 37 | 38 | 39 | 40 | 41 | 42 |
| | Sample No. | 31R | 32R | 33R | 34R | 35R | 36R | 37R | 38R | 39R | 40R | 41R | 42R |
| Right cheek pouch, oral mucosa | | 0 | 0 | 0 | 0 | 0 | 0 | 0 | 0 | 0 | 0 | 0 | 0 |
| Epithelium (cell degeneration, metaplasia, or erosion) | | 0 | 0 | 0 | 0 | 0 | 0 | 0 | 0 | 0 | 0 | 0 | 0 |
| Leukocyte infiltration | | 0 | 0 | 0 | 0 | 0 | 0 | 0 | 0 | 0 | 0 | 0 | 0 |
| Vascular congestion | | 0 | 0 | 0 | 0 | 0 | 0 | 0 | 0 | 0 | 0 | 0 | 0 |
| Edema | | 0 | 0 | 0 | 0 | 0 | 0 | 0 | 0 | 0 | 0 | 0 | 0 |
| Inflammation index | | 0 | 0 | 0 | 0 | 0 | 0 | 0 | 0 | 0 | 0 | 0 | 0 |
| Average grade | | | | | | | 0 | | | | | | |
| Other manifestations | | | | | | | | | | | | | |
| Intercellular edema | | − | − | − | − | − | − | − | − | − | − | − | − |
| Increased keratosis | | − | − | − | − | − | − | − | − | − | − | − | − |
| Intraepidermal microabscess | | − | − | − | − | − | − | − | − | ± | − | | |

Grade in other manifestations −: within normal limited, ±: very slight, +: slight, 2+: moderate, 3+: severe

[Fig. 13]
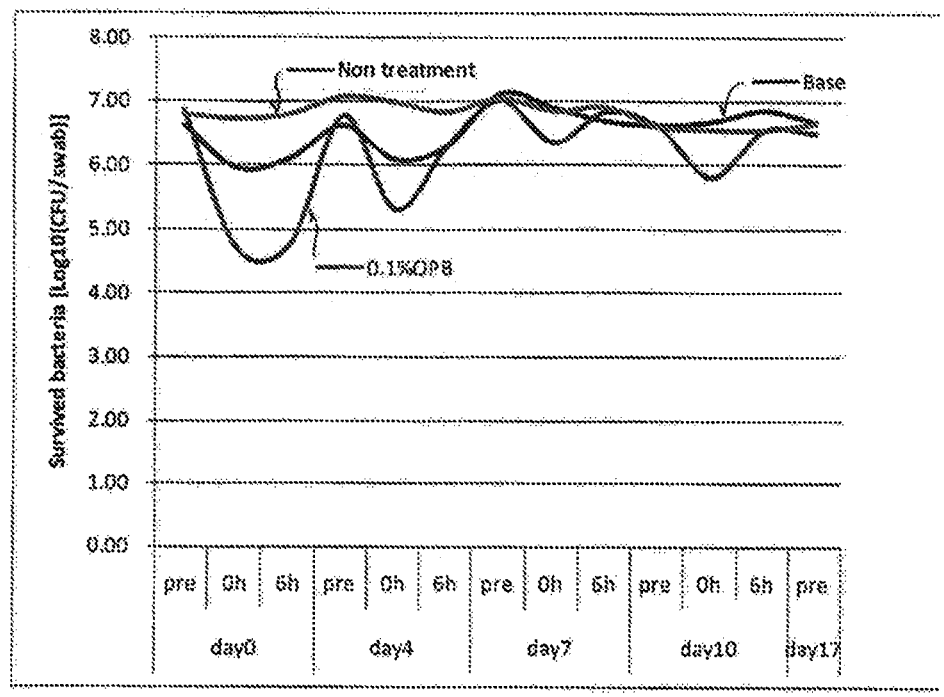
[Fig. 14]
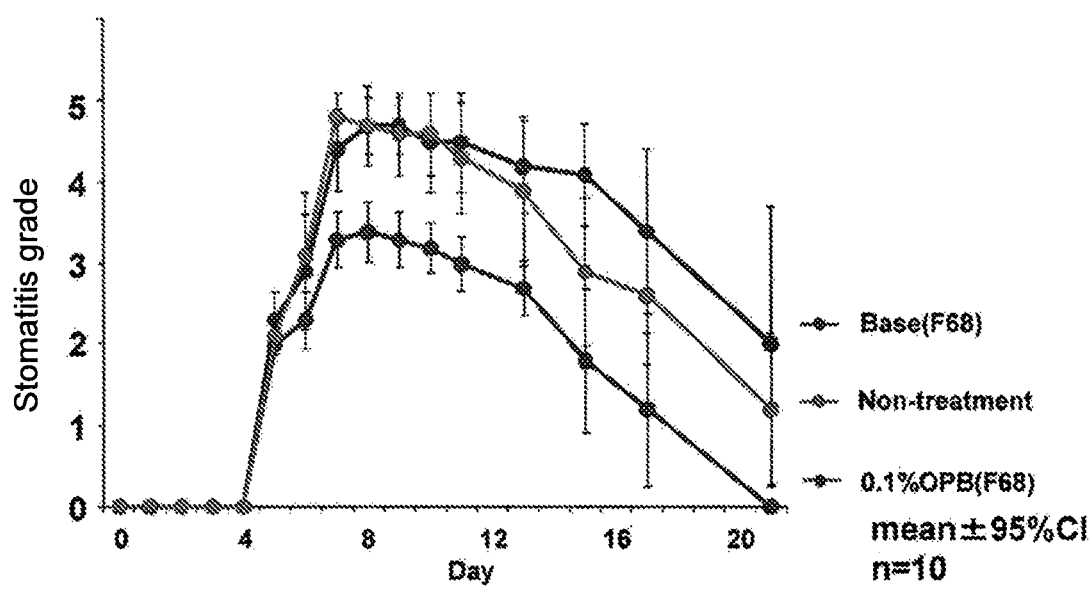

[Fig. 15]
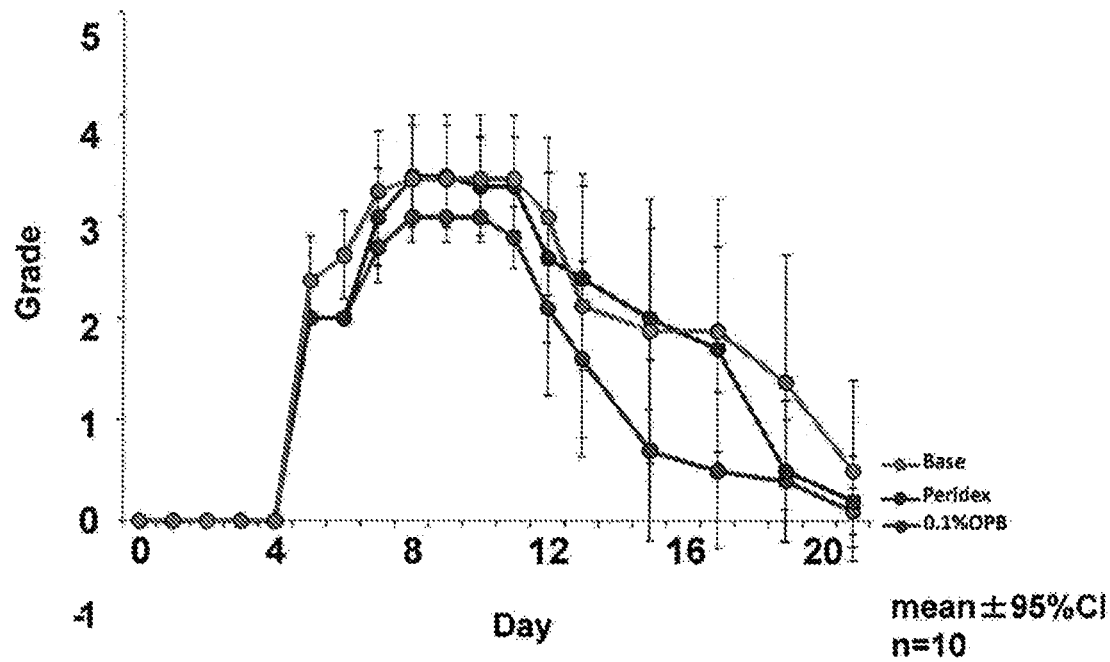
[Fig. 16]
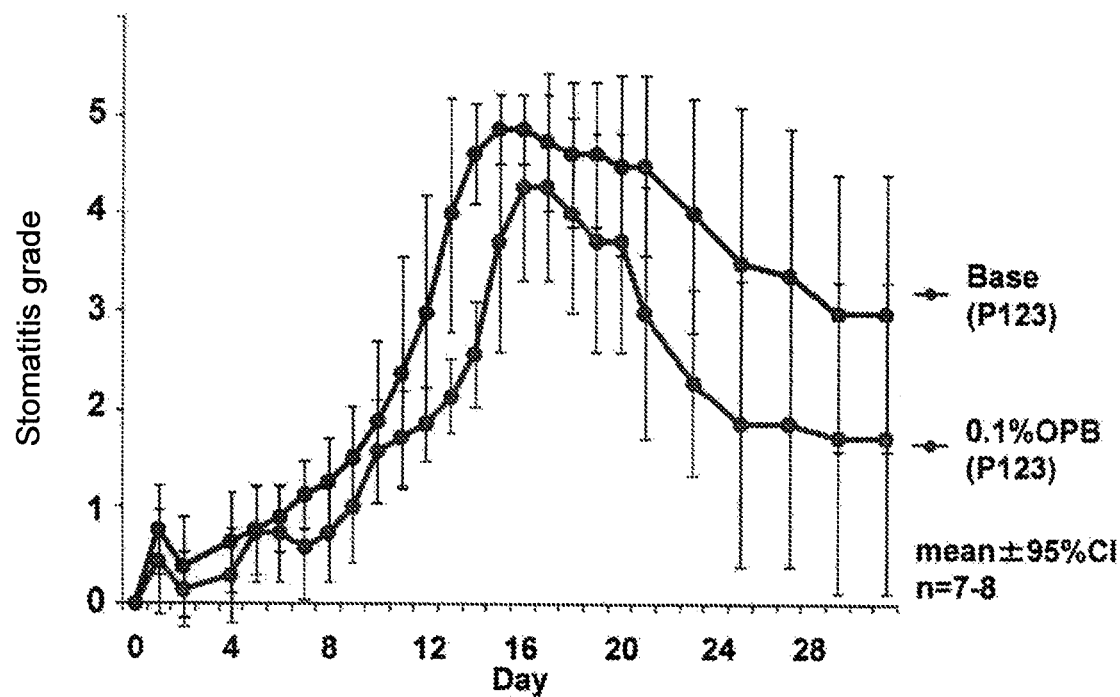

[Fig. 17]

| Organ: Histopathological manifestation | Group Animal No. | OPB | | | | | | | | | | Base | | | | | | | | | |
|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 |
| Stratified squamous epithelium, gingiva | | | | | | | | | | | | | | | | | | | | | |
|   Neutrophil infiltration | | − | ± | ± | − | ± | ± | ± | ± | ± | ± | ± | ± | ± | + | ± | ± | ± | ± | ± | + |
|   Intercellular edematization | | − | − | − | − | − | ± | − | − | − | − | − | − | − | ± | ± | − | − | − | − | − |
|   Hyperkeratosis | | − | − | − | − | − | − | − | − | − | − | − | − | − | − | ± | − | ± | − | − | − |
|   Acanthosis | | − | − | − | − | − | − | − | − | − | − | − | − | − | ± | − | − | ± | − | − | − |
|   Erosion | | − | − | ± | − | − | − | − | − | − | − | − | − | − | − | − | ± | − | − | − | − |
| Basal lamina, gingiva | | | | | | | | | | | | | | | | | | | | | |
|   Neutrophil infiltration | | ± | ± | ± | ± | ± | ± | ± | ± | − | − | ± | ± | − | + | ± | + | ± | ± | ± | + |
|   Bleeding | | − | − | ± | − | − | − | − | − | − | − | − | − | − | − | − | − | − | − | − | ± |
|   Edematization | | − | − | − | − | − | − | − | − | − | − | − | − | − | ± | − | − | − | − | − | − |

Grade; −: negative, ±: very slight, +: slight, 2+: moderate, 3+:severe

[Fig. 18]

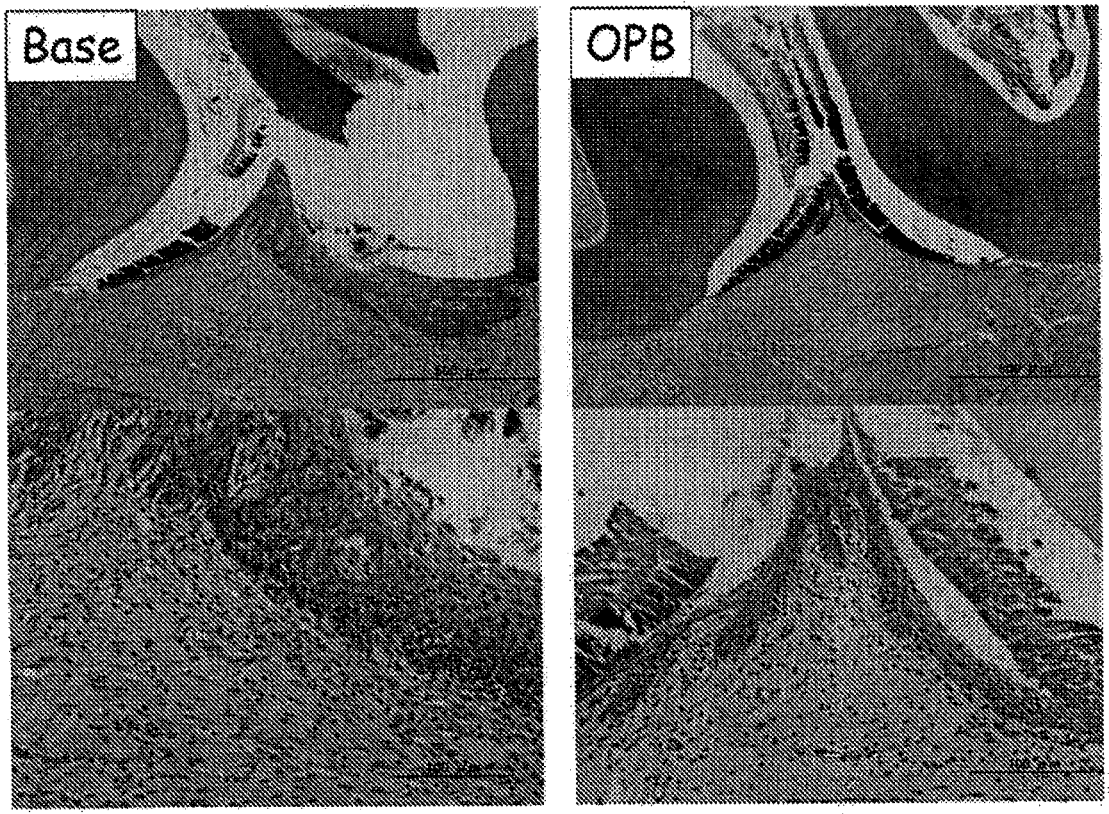

[Fig. 19]

| Administration solution | Time point | Animal No | Amount of BALF collected (mL) | WBC 10²/uL | NEUT 10²/uL | LDH U/L | LDH (ELISA) IU/L | IL-6 pg/mL | TNF-a pg/mL | WBC 10²/uL | NEUT 10²/uL | LDH U/L | IL-6 U/L | TNF-a U/L |
|---|---|---|---|---|---|---|---|---|---|---|---|---|---|---|
| OPB | 6h | 1 | 22 | 368.6 | 300.1 | 27.0 | 0.28 | 2052.1 | 1410.7 | 362.4 | 285.3 | 47.5 | 1787.7 | 1243.4 |
| | | 2 | 22.5 | 268.7 | 208.9 | 24.0 | 0.18 | 438.8 | 158.0 | | | | | |
| | | 3 | 21.5 | 334.5 | 253.9 | 40.0 | 0.42 | 1389.8 | 1068.1 | | | | | |
| | | 4 | 20 | 380.4 | 339.0 | 98.0 | 2.86 | 2520.0 | 1488.9 | | | | | |
| | | 5 | 19 | 379.2 | 303.8 | 58.0 | 1.01 | 1719.4 | 1150.0 | | | | | |
| | | 6 | 22.5 | 445.0 | 305.8 | 40.0 | 0.60 | 2606.5 | 2204.6 | | | | | |
| | 24h | 7 | 18.5 | 64.2 | 49.1 | 129.0 | 4.98 | 95.4 | 5.9 | 159.6 | 124.5 | 120.7 | 95.9 | 8.8 |
| | | 8 | 23 | 150.9 | 121.0 | 107.0 | 2.58 | 83.3 | 7.1 | | | | | |
| | | 9 | 21.5 | 185.9 | 141.9 | 78.0 | 1.20 | 107.5 | 17.7 | | | | | |
| | | 10 | 22 | 212.7 | 166.0 | 65.0 | 1.01 | 89.6 | 7.7 | | | | | |
| | | 11 | 20 | 134.3 | 106.8 | 190.0 | 9.04 | 104.1 | 9.5 | | | | | |
| | | 12 | 22 | 209.4 | 182.1 | 157.0 | 5.26 | 95.4 | 4.6 | | | | | |
| Base | 6h | 13 | 20 | 271.5 | 188.3 | 102.0 | 3.27 | 3141.7 | 4658.4 | 388.9 | 298.3 | 56.0 | 2380.0 | 4291.7 |
| | | 14 | 21.5 | 343.3 | 266.6 | 25.0 | 0.18 | 1797.6 | 2048.5 | | | | | |
| | | 15 | 21 | 486.7 | 378.7 | 35.0 | 0.51 | 3846.3 | 5423.6 | | | | | |
| | | 16 | 17.5 | 205.4 | 145.9 | 93.0 | 3.41 | 811.4 | 1430.1 | | | | | |
| | | 17 | 20 | 693.2 | 529 | 50 | 1.29 | 2090.8 | 6774.2 | | | | | |
| | | 18 | 19 | 333.0 | 281.2 | 31 | 0.37 | 2591.9 | 5415.2 | | | | | |
| | 24h | 19 | 22.5 | 272.1 | 213.5 | 60 | 0.60 | 203.7 | 77.6 | 259.8 | 186.3 | 128.7 | 253.3 | 98.8 |
| | | 20 | 20 | 276.2 | 199.5 | 150 | 6.55 | 289.6 | 82.3 | | | | | |
| | | 21 | 20 | 183.6 | 120.5 | 151 | 6.69 | 1912 | 59.8 | | | | | |
| | | 22 | 20 | 296.1 | 190.5 | 174 | 10.15 | 299.9 | 125.0 | | | | | |
| | | 23 | 22 | 276.5 | 213.4 | 74 | 1.57 | 123.4 | 154.7 | | | | | |
| | | 24 | 20 | 254.5 | 180.5 | 151 | 7.93 | 411.8 | 93.1 | | | | | |

[Fig. 20]
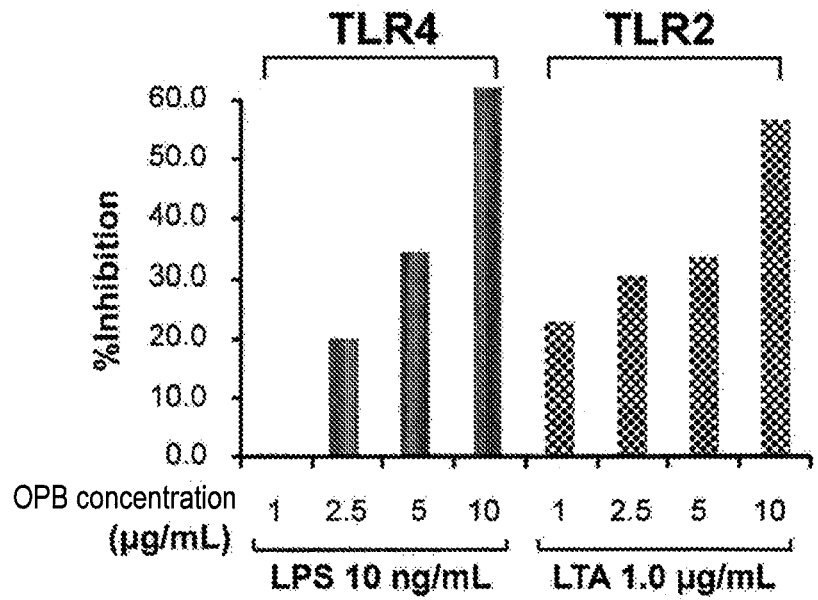
[Fig. 21]
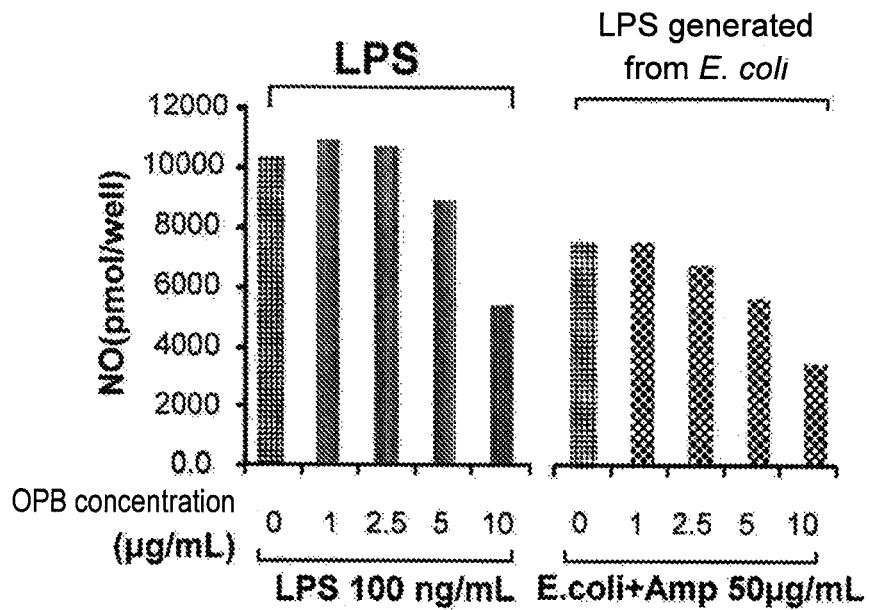

METHOD OF TREATING AND/OR PREVENTING INFLAMMATION BY ADMINISTERING OLANEXIDINE

TECHNICAL FIELD

The present invention relates to an anti-inflammatory agent comprising olanexidine or a pharmacologically acceptable salt thereof as an active ingredient.

BACKGROUND ART

Olanexidine is a compound, called 1-(3,4-dichlorobenzyl)-5-octylbiguanide under chemical name, having high bactericidal activity. Olanexidine gluconate, which is a gluconate thereof, has a wide bactericidal spectrum. Its bactericidal effect appears in a short time, and further, the activity persists for a long time. Moreover, an aqueous solution of olanexidine gluconate is highly stable, can be preserved for a long period, furthermore is low irritant or toxic to the skin, and is also excellent in safety. In addition, the aqueous solution of olanexidine gluconate is free from problems with color, odor and taste and as such, is easily produced as drug formulation (patent document 1). Hence, olanexidine gluconate is mainly used in the antisepsis of the skin at an operation site (field of operation).

However, it has not been known so far that olanexidine or a salt thereof exhibits anti-inflammatory action. Moreover, since olanexidine gluconate has irritancy to the mucosa, the olanexidine gluconate is difficult to apply to the mucosa such as the oral mucosa.

PRIOR ART DOCUMENT

Patent Document
Patent document 1: Japanese unexamined Patent Application Publication No. 2005-289959

SUMMARY OF THE INVENTION

Object to be Solved by the Invention

An object of the present invention is to provide a composition that can be used as a novel anti-inflammatory agent.

Means to Solve the Object

The present inventors have conducted diligent studies to attain the object and consequently found that, unexpectedly, olanexidine or a salt thereof exhibits anti-inflammatory action. The present inventors have further found that olanexidine gluconate is applicable to the mucosa such as the oral mucosa by using a composition comprising the olanexidine gluconate and a poloxamer which is a block copolymer consisting of a chain of polyoxypropylene (POP) and two chains of polyoxyethylene (POE) flanking the POP, leading to the completion of the present invention.

Specifically, the present invention is as follows.
(1) A composition for amelioration and/or prevention of an inflammation, comprising olanexidine or a pharmacologically acceptable salt thereof.
(2) The composition according to (1), wherein the olanexidine or the pharmacologically acceptable salt thereof is olanexidine gluconate.
(3) The composition according to (1) or (2), further comprising a poloxamer which is a block copolymer consisting of a chain of polyoxypropylene (POP) and two chains of polyoxyethylene (POE) flanking the POP.
(4) The composition according to any one of (1) to (3), wherein the inflammation is selected from stomatitis, oral mucositis, gingivitis, and pneumonia.
(5) The composition according to any one of (1) to (4), wherein
the inflammation is oral mucositis due to treatment of a cancer, and
the composition comprises
0.01 to 1.5% (W/V) of olanexidine gluconate, and
a poloxamer which is a block copolymer consisting of a chain of polyoxypropylene (POP) and two chains of polyoxyethylene (POE) flanking the POP.
(6) The composition according to any one of (3) to (5), wherein the poloxamer is selected from polyoxyethylene (42) polyoxypropylene (67) glycol (Pluronic P-123), polyoxyethylene (54) polyoxypropylene (39) glycol (Pluronic P-85), and polyoxyethylene (196) polyoxypropylene (67) glycol (Pluronic F-127).
(7) The composition according to (6), wherein the poloxamer is polyoxyethylene (42) polyoxypropylene (67) glycol (Pluronic P-123).
(8) The composition according to any one of (1) to (7), wherein a concentration of the olanexidine gluconate is 0.05 to 0.5% (W/V).
(9) The composition according to any one of (3) to (8), wherein a concentration of the poloxamer is 0.1 to 5.0% (W/V).
(10) The composition according to any one of (1) to (9), wherein the composition is in a form of a liquid or a gargle.
(11) The composition according to any one of (5) to (10), wherein the treatment of the cancer is chemotherapy, radiotherapy, or concurrent chemoradiotherapy.

Other examples of the mode of carrying out the present invention can include a method for ameliorating or preventing (treating) an inflammation by administering the composition for amelioration and/or prevention of an inflammation of the present invention to a patient in need of amelioration or prevention (treatment) of an inflammation, a method for ameliorating or preventing (treating) oral mucositis due to treatment of a cancer by administering the composition for amelioration and/or prevention of oral mucositis due to treatment of a cancer of the present invention to a patient in need of amelioration or prevention (treatment) of oral mucositis due to treatment of a cancer, a composition comprising olanexidine or a pharmacologically acceptable salt thereof for use in amelioration or prevention (treatment) of an inflammation, a composition comprising 0.01 to 1.5% (W/V) of olanexidine gluconate, and a poloxamer which is a block copolymer consisting of a chain of polyoxypropylene (POP) and two chains of polyoxyethylene (POE) flanking the POP for use in amelioration or prevention (treatment) of oral mucositis due to treatment of a cancer, use of olanexidine or a pharmacologically acceptable salt thereof for preparing the composition for amelioration and/or prevention of an inflammation of the present invention, and use of 0.01 to 1.5% (W/V) of olanexidine gluconate, and a poloxamer which is a block copolymer consisting of a chain of polyoxypropylene (POP) and two chains of polyoxyethylene (POE) flanking the POP for preparing the composition for amelioration and/or prevention of oral mucositis due to treatment of a cancer of the present invention.

Effect of the Invention

The present invention provides a novel composition for amelioration and/or prevention of an inflammation. The composition of the present invention is applicable to a wide range of inflammations such as stomatitis, oral mucositis, gingivitis, and pneumonia. Moreover, the composition for amelioration and/or prevention of an inflammation (anti-inflammatory agent) of the present invention can ameliorate and/or prevent oral mucositis in a patient who is receiving chemotherapy, radiotherapy, or concomitant chemotherapy and radiotherapy of a cancer, and thus, can prevent reduction in QOL, such as inhibition of a communication function, sleep disorder, pain, or dysphagia (decreased dietary intakes), in a patient, or disturbance of dose conformity of chemotherapy and/or radiotherapy.

BRIEF DESCRIPTION OF DRAWINGS

FIG. 1 is a diagram showing results of measuring the number of bacteria in the oral cavity by aerobic culture in Example 1. The number of bacteria in the ordinate was indicated by a logarithmic value.

FIG. 2 is a diagram showing results of measuring the number of bacteria in the oral cavity by culture in a *streptococcus* selective medium in Example 1. The number of bacteria in the ordinate was indicated by a logarithmic value.

FIG. 3 is a diagram showing results of measuring the number of bacteria in the oral cavity by anaerobic culture in Example 1. The number of bacteria in the ordinate was indicated by a logarithmic value.

FIG. 4 is a diagram showing results of measuring the number of bacteria in the oral cavity using a bacterial counter in Example 1. The number of bacteria in the ordinate was indicated by a logarithmic value.

FIG. 5 is a diagram showing results of a comparison test between Olanedine® antiseptic solutions (OPB) and other agents in Example 2. The number of bacteria in the ordinate was indicated by a logarithmic value.

FIG. 6 is a diagram showing results of studying the influence of an olanexidine concentration on bactericidal efficacy in Example 3. The number of bacteria in the ordinate was indicated by a logarithmic value.

FIG. 7 is a diagram showing change in body weight of each group in Example 4.

FIG. 8 is a table showing macroscopic observation results in Example 4. The numeric values in the table represent stomatitis grades, and the shaded areas represent groups presenting with a leukoplakia-like symptom (increased keratosis, thickening, etc.).

FIG. 9 is a photograph of the cheek pouch of each group on the final day in Example 4.

FIG. 10 is a table showing histopathological examination results in Example 4.

FIG. 11 is a table showing macroscopic observation results in Example 5. The numeric values in the table represent stomatitis grades, and the shaded areas represent groups presenting with a leukoplakia-like symptom (increased keratosis, thickening, etc.).

FIG. 12 is a table showing histopathological examination results in Example 5.

FIG. 13 is a diagram showing the number of surviving bacteria in the hamster oral cavity in Example 6. The number of bacteria in the ordinate was indicated by a logarithmic value.

FIG. 14 is a diagram showing a stomatitis grade in Example 6. The stomatitis grade is shown in the ordinate.

FIG. 15 is a diagram showing a stomatitis grade in Example 7. The stomatitis grade is shown in the ordinate.

FIG. 16 is a diagram showing a stomatitis grade in Example 8. The stomatitis grade is shown in the ordinate.

FIG. 17 is a diagram showing pathological examination results in Example 9.

FIG. 18 is a micrograph of a HE-stained specimen in Example 9.

FIG. 19 is a diagram showing results of hematological examination and biochemical examination in Example 10.

FIG. 20 is a diagram showing the inhibition rate of SEAP expression by an Olanedine® antiseptic solution (OPB) in Example 11.

FIG. 21 is a diagram showing the inhibition of NO production by an Olanedine® antiseptic solution (OPB) in Example 12.

MODE OF CARRYING OUT THE INVENTION

The composition of the present invention is a composition for amelioration and/or prevention of an inflammation, comprising olanexidine or a pharmacologically acceptable salt thereof. A salt pharmacologically known in the art can be used as the pharmacologically acceptable salt of olanexidine. Examples thereof can include hydrochloride, carbonate, bicarbonate, citrate, gluconate, lactate, acetate, gluceptate, and tartrate. Olanexidine gluconate is preferred from the viewpoint of solubility in water.

In the composition of the present invention, olanexidine can be contained at a concentration that can exhibit anti-inflammatory action. Examples thereof can include 0.001 to 20% (W/V), preferably 0.005 to 15% (W/V), more preferably 0.01 to 10% (W/V), further preferably 0.1 to 5% (W/V), in terms of olanexidine gluconate. In the case of applying the composition of the present invention to the mucosa such as the oral mucosa, the concentration of olanexidine is preferably 0.01 to 1.5% (W/V), more preferably 0.05 to 0.5% (W/V), further preferably 0.1 to 0.3% (W/V), in terms of olanexidine gluconate. In the case of applying the composition of the present invention to the oral mucosa, it is not desirable that bactericidal efficacy on oral bacteria cannot be sufficiently obtained if the concentration of olanexidine gluconate is lower than 0.01% (W/V), and irritation to the oral mucosa is too strong if the concentration of olanexidine gluconate exceeds 1.5% (W/V).

The composition of the present invention may further comprise one or more poloxamers in order to reduce irritation to an application site. In this context, the poloxamer is not particularly limited as long as the poloxamer is a block copolymer consisting of a chain of polyoxypropylene (POP) and two chains of polyoxyethylene (POE) flanking the POP, and reduces irritation to an application site. One or more poloxamers selected from polyoxyethylene (42) polyoxypropylene (67) glycol (Pluronic P-123), polyoxyethylene (54) polyoxypropylene (39) glycol (Pluronic P-85), and polyoxyethylene (196) polyoxypropylene (67) glycol (Pluronic F-127) are preferred. Among others, examples thereof can include polyoxyethylene (42) polyoxypropylene (67) glycol (Pluronic P-123), polyoxyethylene (3) polyoxypropylene (17) glycol (Pluronic L-31), polyoxyethylene (20) polyoxypropylene (20) glycol (Pluronic L-44), polyoxyethylene (120) polyoxypropylene (40) glycol (Pluronic F-87), and polyoxyethylene (160) polyoxypropylene (30) glycol (Pluronic F-68).

Among the poloxamers described above, one or more poloxamers selected from polyoxyethylene (42) polyoxypropylene (67) glycol (Pluronic P-123), polyoxyethylene (54) polyoxypropylene (39) glycol (Pluronic P-85), and polyoxyethylene (196) polyoxypropylene (67) glycol (Pluronic F-127) are preferred. Among them, polyoxyethylene (42) polyoxypropylene (67) glycol (Pluronic P-123) is more preferred.

Examples of the concentration of the poloxamer can include, but are not particularly limited to, 0.1 to 5.0% (W/V), preferably 0.1 to 4.0% (W/V), more preferably 0.1 to 3.0% (W/V), further preferably 0.1 to 2.0% (W/V), most preferably 0.1 to 1.5% (W/V). The concentration ratio between olanexidine gluconate and the poloxamer is preferably 1:2 to 1:20, more preferably 1:5 to 1:10. In the case of applying the composition of the present invention to the oral mucosa, irritation of the oral mucosa by olanexidine gluconate is strong in a high concentration range equal to or higher than an olanexidine gluconate concentration of 0.3% (W/V). Therefore, a larger amount of the poloxamer is more preferred for suppressing irritation (increased keratosis) by olanexidine gluconate.

In the present specification, the "inflammation" means biological reaction causing a sign such as flare, a feeling of warmth, swelling, or pain due to an internal factor such as autoimmune disease, or an external factor such as bacterial or viral infection, trauma, physical irritation (heat, coldness, radiation, electricity, etc.), or a chemical substance. The inflammation according to the present invention is not particularly limited as long as the composition of the present invention can be applied to the inflammation. Examples thereof can preferably include an inflammation involving a Toll-like receptor, more preferably an inflammation due to bacterial infection. Examples of the inflammation site can include the brain, the eye, the trachea, a vascular vessel, the lung, the liver, the heart, the pancreas, the stomach, the intestine, the mesenterium, the kidney, the skin, the nasal mucosa, the oral mucosa, the gingiva and the joint. Specific examples of the inflammation can include encephalitis, bronchitis, angiitis, pneumonia, hepatitis, myocarditis, pancreatitis, enteritis, gastritis, peritonitis, nephritis, stomatitis, oral mucositis, gingivitis, arthritis, an inflammation caused by reperfusion injury after ischemia, an inflammation caused by immune rejection after transplantation, an inflammation caused by burn or multiple organ failure, inflammation developed after operation, and an inflammation caused by arteriosclerosis. Among them, preferred examples thereof can include stomatitis, oral mucositis, gingivitis, and pneumonia. In the present specification, the oral mucositis refers to an inflammation developed in the oral mucosa by treatment of a cancer, and the stomatitis refers to an inflammation developed in the oral mucosa independently of treatment of a cancer. Alternatively, the composition of the present invention may be a composition having a specific purpose of ameliorating and/or preventing oral mucositis due to treatment of a cancer. In one aspect, the present invention excludes a composition having a purpose of ameliorating and/or preventing oral mucositis due to treatment of a cancer.

The composition of the present invention can be applied to the skin, the oral mucosa, or the mucosa of the gingiva, the gastrointestinal tract, the trachea, the lung, or the like at an inflammation site. Examples of the administration method can include injection (intravenous, intramuscular, subcutaneous, intracutaneous, intraperitoneal, etc.), oral administration, percutaneous administration, inhalation, embrocation to the oral cavity, embrocation to the gingiva, and gargling. Preparations can be appropriately produced according to these administration methods. A selectable dosage form is not particularly limited, and the dosage form can be widely selected from, for example, an injection (a solution, a suspension, an emulsion, a solid formulation for dissolution in use, etc.), a tablet, a capsule, a granule, a powder, a liquid, a gargle, a liposome formulation, an ointment, a gel, a power for external use, a spray, and an inhalation powder. Also, components usually used in medicaments, such as a common excipient, stabilizer, binder, lubricant, emulsifier, osmotic pressure adjuster, pH adjuster, colorant, and disintegrant can be used for preparing these drug formulations.

In the case of applying the composition of the present invention to the oral cavity, any dosage form suitable for application to the oral cavity may be used. Preferred examples thereof can include a liquid and a gargle. Alternatively, a solid composition gradually dissolving or disintegrating in the mouth, such as lozenges, candies, gummy candies, troches, or gums, may be used. Moreover, if necessary, the composition of the present invention can further contain various additives that are used for the purpose of conferring flavor or coloring. Examples of the additive for the purpose of conferring flavor can include a synthetic fragrance, a natural fragrance, and a sweetener such as aspartame, acesulfame potassium, sucralose, alitame, neotame, a licorice root extract (glycyrrhizin), saccharin, saccharin sodium, a stevia extract, and a stevia powder. Examples of the additive for the purpose of coloring can include caramel, a natural coloring agent, and a synthetic coloring agent. Also, the composition of the present invention may contain an additive such as an emulsifier (glycerin fatty acid ester, sorbitan fatty acid ester, propylene glycol fatty acid ester, sucrose fatty acid ester, lecithin, etc.), a stabilizer, or a preservative. These additive agents may be used alone or in combination of two or more thereof.

In the case of administering the composition of the present invention as a liquid or a gargle, a single dose can be arbitrarily determined depending on a site where an inflammation has been developed, or severity. Examples thereof can include 1 to 100 mL, preferably 2 to 50 mL, more preferably 5 to 40 mL, most preferably 10 to 30 mL.

The timing of administration of the composition of the present invention can be arbitrarily determined depending on a site where an inflammation has been developed, severity, or the degree of amelioration of an inflammation. Examples thereof can include after eating, after wake-up, and before bedtime. Alternatively, the composition of the present invention may be administered at intervals of 2 to 8 hours, preferably at intervals of 4 to 6 hours. Also, the composition of the present invention can prevent an inflammation by administration to a patient before operation or a patient after oral care.

The administration period of the composition of the present invention can be arbitrarily determined depending on the degree of amelioration of an inflammation. Examples thereof can include 1 week to 3 months, preferably 1 week to 2 months, more preferably 1 week to 1 month, most preferably 1 to 2 weeks.

In the present invention, examples of the treatment of the cancer can include chemotherapy, radiotherapy, and concurrent chemoradiotherapy of the cancer. The chemotherapy of the cancer refers to general treatment of the cancer with an anticancer agent. Examples of the anticancer agent used in the present invention can include a pyrimidine fluoride-based antimetabolite such as fluorouracil (5-FU), tegafur/gimeracil/oteracil potassium (S-1), and tegafur/uracil (UFT), a folate antagonist such as methotrexate, an antitumor antibiotic such as daunorubicin, doxorubicin, epirubicin, bleomycin, peplomycin, and actinomycin D, a vegetable alkaloid such as paclitaxel, docetaxel, vincristine, and etoposide, and a platinum-containing drug such as cisplatin, carboplatin, and nedaplatin, which easily cause oral mucositis. Particularly preferred examples thereof can include a pyrimidine fluoride-based antimetabolite such as 5-FU. These anticancer agents may be used alone or in combination of two or more thereof.

In the present invention, the radiotherapy is a treatment for the purpose of suppressing proliferation of cancer cells by irradiating a malignant tumor portion with radiation. Examples of the radiation for use in the treatment include an X-ray and an electron beam. The concurrent chemoradiotherapy refers to a treatment method that enhances the effect of radiation by using radiation therapy, which is a local cancer therapy, and an anticancer agent in combination. The target site of the radiotherapy is not particularly limited. Examples of the radiotherapy can include radiotherapy in the head and neck portion, particularly, in the oral cavity or the pharyngeal portion.

Hereinafter, the present invention will be described more specifically with reference to Examples. However, the technical scope of the present invention is not limited by these examples.

Example 1

1. Test on Bactericidal Efficacy in Oral Cavity Using Cynomolgus Monkey

In this test, bactericidal efficacy on bacteria in the oral cavity of cynomolgus monkeys was compared and studied by using a simplified bacterial counter and a culture technique in combination, and using test materials (0.1% (w/v) olanexidine gluconate and 0.47% povidone-iodine as bactericidal antiseptics, and saline as a negative control drug).

1-1 Test Material

A test substance was prepared by diluting Olanedine® Antiseptic Solution 1.5% (hereinafter, referred to as "1.5% OPB", etc.; a solution containing 1.508% (w/v) of olanexidine gluconate, manufactured by Otsuka Pharmaceutical Factory, Inc.) 15-fold such that the olanexidine gluconate concentration was 0.1% (w/v) (0.1% OPB). A control substance Isodine Gargle Solution 7% (hereinafter, referred to as "7% PVP-I", etc.; manufactured by Meiji Seika Pharma Co., Ltd.) was diluted 15-fold (0.47% PVP-I), and saline (manufactured by Otsuka Pharmaceutical Factory, Inc.) was used as it was.

1-2 Test Animal

Cynomolgus monkeys (male, produced in Cambodia, manufactured by EveBioscience Co., Ltd.) which were 2 years and 11 months to 3 years and 11 months old when used, were used.

1-2-1 Group Configuration

The oral cavity of each animal was used as a test site. Nine animals were used, and the number of test sites per group was set to 3 in order to embrocate 0.1% OPB, 0.47% PVP-I and saline. Bacteria were collected a total of 4 times (before test material embrocation, and 10 minutes, 6 hours and 24 hours after embrocation).

1-2-2 Animal Number and Sample Number

Animal numbers and sample numbers were assigned as shown in Table 1 below. The numbers of baseline bacteria of animal Nos. 1 to 3 were measured, and the animals were subjected to tests using saline, 0.1% OPB, and 0.47% PVP-I in descending order of the number of bacteria. Likewise, animal Nos. 4 to 6 were subjected to tests using 0.1% OPB, 0.47% PVP-I, and saline in descending order of the number of bacteria, and animal Nos. 7 to 9 were subjected to tests using 0.47% PVP-I, saline, and 0.1% OPB in descending order of the number of bacteria.

TABLE 1

| Sample No. | Animal No. | Time point |
|---|---|---|
| 1 | 1 | baseline |
| 2 |   | 10 min |
| 3 |   | 6 hr |
| 4 |   | 24 hr |
| 5 | 2 | baseline |
| 6 |   | 10 min |
| 7 |   | 6 hr |
| 8 |   | 24 hr |
| 9 | 3 | baseline |
| 10 |   | 10 min |
| 11 |   | 6 hr |
| 12 |   | 24 hr |
| 13 | 4 | baseline |
| 14 |   | 10 min |
| 15 |   | 6 hr |
| 16 |   | 24 hr |
| 17 | 5 | baseline |
| 18 |   | 10 min |
| 19 |   | 6 hr |
| 20 |   | 24 hr |
| 21 | 6 | baseline |
| 22 |   | 10 min |
| 23 |   | 6 hr |
| 24 |   | 24 hr |
| 25 | 7 | baseline |
| 26 |   | 10 min |
| 27 |   | 6 hr |
| 28 |   | 24 hr |
| 29 | 8 | baseline |
| 30 |   | 10 min |
| 31 |   | 6 hr |
| 32 |   | 24 hr |
| 33 | 9 | baseline |
| 34 |   | 10 min |
| 35 |   | 6 hr |
| 36 |   | 24 hr |

1-3 Testing Method 1-3-1 Anesthesia

The cynomolgus monkeys were systemically anesthetized by intramuscularly injecting a 2:1 mixed solution of Ketalar (50 mg/mL in terms of ketamine, manufactured by Daiichi Sankyo Propharma Co., Ltd.) and Seractal 2% Injection Solution (2.0 g/100 mL in terms of xylazine, manufactured by Bayer Yakuhin, Ltd.) at 0.5 mL per kg of body weight.

1-3-2 Embrocation

[1] 100 mL of each test material was poured to a container (250 mL, manufactured by Corning Inc.) in which two Mouth Pure Oral Care Sponges (manufactured by Kawamoto Corp.) were placed.

[2] The air was evacuated from the sponges, and the sponges were sufficiently soaked in the test material.

[3] The resultant was embrocated to the oral cavity for approximately 2 minutes.

1-3-3 Bacterial Collection 1

[1] Bacteria were collected from the monkey oral cavity using a sterilized glove and a sterile swab (both the lateral walls in the oral cavity were scrubbed back and forth twice).

[2] The swab was placed in 5 mL of a sampling solution (10% (w/v) polysorbate 80, 0.04% (w/v) potassium dihydrogen phosphate, 0.1% (w/v) Triton X-100, 1.01% (w/v) anhydrous sodium monohydrogen phosphate, 2% (w/v) soybean lecithin, 5% (w/v) polyoxyethylene (20) cetyl ether, pH 7.8 to 7.9).

1-3-4 Bacterial Collection 2

[1] A swab of expendable supplies for measurement (DU-AC02NP-H, manufactured by Panasonic Healthcare Co., Ltd.) was fitted into a constant-pressure sample collection instrument (DU-AE01NT-H, manufactured by Panasonic Healthcare Co., Ltd.).

[2] The swab was pressured with constant pressure against the monkey tongue, which was then scrubbed back and forth three times at intervals of approximately 1 cm.

1-3-5 Measurement of the Number of Bacteria in Oral Cavity by Plate Culture Technique The agar plate pouring technique and the agar plate surface smearing technique were carried out with reference to New GMP Microbial Testing Methods and Standard Methods of Analysis in Food Safety Regulation.

[1] Each sampling solution into which the bacteria were recovered in 1-3-3 was vigorously stirred, and the resultant was used as a recovered bacterial suspension.

[2] 0.5 mL of the recovered bacterial suspension was diluted 10-fold, and dilution was further repeated by similar manipulation to make 10-fold dilution series (5 scales).

[3] 1 mL each of the recovered bacterial suspension and the serial dilutions was dispensed to each dish. Approximately 15 mL of a measurement medium (TSA+) preserved at approximately 47° C. was added thereto to make pour plates. Also, 100 μL each of the recovered bacterial suspension and the serial dilutions was dispensed to each blood agar medium or each MS agar medium, and the surface was smeared using a bacteria spreader.

[4] After solidification of the measurement medium (TSA+), the pour plates were inverted, and cultured until colony counting was enabled. Also, the surface-smeared plates were inverted, and cultured under anaerobic conditions until colony counting was enabled.

[5] Colonies that proliferated in the pour plates and the surface-smeared plates were counted using a colony counter (DC-3, AS ONE Corp.). A pour plate in which the number of colonies was too many to distinguish the colonies was regarded as TNTC (too numerous to count) without counting.

1-3-6 Measurement of the Number of Bacteria in Oral Cavity Using Bacterial Counter

[1] A bacterial counter (DU-AA01, manufactured by Panasonic Healthcare Co., Ltd.) was opened up.

[2] A sensor chip of expendable supplies for measurement was fitted into the bacterial counter.

[3] A disposable cup of the expendable supplies for measurement was loaded in the bacterial counter.

[4] A swab into which bacteria were collected was loaded to the center of the disposable cup.

[5] The bacterial counter was closed.

1-4 Results 1-4-1 Measurement of the Number of Bacteria in Oral Cavity by Plate Culture Technique (1) Aerobic Culture The results are shown in FIG. 1. The number of baseline bacteria in the oral cavity was $1.73 \times 10^5$ to $4.20 \times 10^6$. The number of bacteria in the oral cavity after saline embrocation was almost constant. The number of viable bacteria was $6.48 \times 10^5$ CFU, $4.65 \times 10^3$ CFU and $2.35 \times 10^4$ CFU 10 minutes after test material embrocation, $1.66 \times 10^6$ CFU, $1.47 \times 10^3$ CFU and $4.93 \times 10^5$ CFU 6 hours after embrocation, and $4.67 \times 10^5$ CFU, $5.58 \times 10^4$ CFU and $1.22 \times 10^6$ CFU 24 hours after embrocation, for saline, 0.1% OPB and 0.47% PVP-I, respectively.

(2) Culture in *Streptococcus* Selective Medium

The results are shown in FIG. 2. The number of baseline bacteria in the oral cavity was $2.85 \times 10^5$ to $7.60 \times 10^7$. The number of bacteria in the oral cavity after saline embrocation was almost constant. The number of viable bacteria was $1.26 \times 10^6$ CFU, $5.97 \times 10^3$ CFU and $7.33 \times 10^4$ CFU 10 minutes after test material embrocation, $5.51 \times 10^6$ CFU, $2.79 \times 10^4$ CFU and $2.20 \times 10^6$ CFU 6 hours after embrocation, and $1.71 \times 10^6$ CFU, $4.30 \times 10^5$ CFU and $7.81 \times 10^6$ CFU 24 hours after embrocation, for saline, 0.1% OPB and 0.47% PVP-I, respectively.

(3) Anaerobic Culture

The results are shown in FIG. 3. The number of baseline bacteria in the oral cavity was $2.45 \times 10^5$ to $1.65 \times 10^7$. The number of bacteria in the oral cavity after saline embrocation was almost constant. The number of viable bacteria was $2.70 \times 10^6$ CFU, $1.33 \times 10^4$ CFU and $7.33 \times 10^4$ CFU 10 minutes after test material embrocation, $3.22 \times 10^6$ CFU, $1.38 \times 10^4$ CFU and $1.80 \times 10^6$ CFU 6 hours after embrocation, and $1.71 \times 10^6$ CFU, $3.04 \times 10^5$ CFU and $1.40 \times 10^6$ CFU 24 hours after embrocation, for saline, 0.1% OPB and 0.47% PVP-I, respectively.

1-4-2 Measurement of the Number of Bacteria in Oral Cavity Using Bacterial Counter The results are shown in FIG. 4. The number of baseline bacteria in the oral cavity was $1.29 \times 10^6$ to $>1.00 \times 10^8$. The number of viable bacteria was $2.84 \times 10^6$ CFU, $<3.49 \times 10^5$ CFU and $5.09 \times 10^5$ CFU 10 minutes after test material embrocation, $2.04 \times 10^7$ CFU, $5.58 \times 10^5$ CFU and $8.98 \times 10^6$ CFU 6 hours after embrocation, and $4.10 \times 10^7$ CFU, $3.14 \times 10^7$ CFU and $3.14 \times 10^7$ CFU 24 hours after embrocation, for saline, 0.1% OPB and 0.47% PVP-I, respectively.

Results having a similar tendency were obtained in both the measurement of the number of bacteria by the plate culture technique and the measurement of the number of bacteria using a bacterial counter. Namely, the 0.1% OPB group kept the number of bacteria at a low value up to 6 hours after embrocation, whereas the 0.47% PVP-I group merely exhibited an effect up to 10 minutes after embrocation. However, the number of bacteria made recovery 24 hours after embrocation in both the groups. No persistency was observed in the 0.47% PVP-I group probably because PVP-I is susceptible to inactivation by organic matter in the oral cavity. 0.1% OPB was considered to have a more persistent bactericidal antiseptic effect in the oral cavity and be superior therein.

Example 2

2. Bactericidal Test in Oral Cavity Using Hamster—1

This test was aimed at comparatively studying the bactericidal efficacy of a gargle (bactericidal antiseptic) on the mucosa in the oral cavity of normal hamsters with other agents. In order to study the persistency of bactericidal activity, time points were established from after test material gargling to 24 hours later (prior to, immediately after, 8 hours after, and 24 hours after gargling), and the number of bacteria was measured using a bacterial counter and the culture technique.

2-1 Test Material

Test substances and control substances were collectively used as test materials.

2-1-1 Test Substance 1

Designation: 0.1% OPB-1

Formula: olanexidine gluconate . . . 0.10 w/v %

Pluronic L-44 . . . 0.07 w/v %

Pluronic P-123 . . . 1.0 w/v %

2-1-2 Test Substance 2
Designation: 0.1% OPB-2
Formula: olanexidine gluconate . . . 0.10 w/v %
    Pluronic L-44 . . . 0.07 w/v %
    Pluronic P-123 . . . 1.0 w/v %
    Lipidure® . . . 1.0 w/v %
2-1-3 Control Substance 1
Designation/abbreviated name: base/Base
Formula: Pluronic L-44 . . . 0.07 w/v %
    Pluronic P-123 . . . 1.0 w/v %
2-1-4 Control substance 2
Designation/abbreviated name: Peridex®/0.12% CHG
Formula: chlorhexidine gluconate . . . 0.12 w/v %
2-1-5 Control Substance 3
Designation/abbreviated name: Isodine Gargle Solution 0.47%/0.47% PVP-I
Formula: 15-fold dilution of Isodine Gargle Solution 7% (7% PVP-I, manufactured by Meiji Seika Pharma Co., Ltd.)
2-2 Animal Used Male Slc: Syrian hamsters which were 6 weeks old upon receipt were used to conduct a test on 4 animals per group.

2-3 Testing Method
2-3-1 Anesthesia

Gas anesthesia [induction of anesthesia: 3.0 L/min of air with 3% isoflurane (manufactured by Mylan Seiyaku Ltd.), the concentration of continuous anesthesia was appropriately adjusted] was carried out.

2-3-2 Test Material Administration

Each hamster was fixed in the supine position under anesthesia, and 1 mL of each test material was injected to one cheek pouch. Thirty seconds later, the test material was eliminated, and a redundant test material was drawn out of the cheek pouch using a sterile swab.

2-3-3 Bacterial Collection

Bacteria were collected from both the cheek pouches under anesthesia using a sterile swab at a total of 4 time points (before test material administration, 0 hr, 8 hr, and 24 hr). The swab after the collection was dipped in 5 mL of a SCDLP medium, then stirred, and used as a sample for bacterial counting.

2-3-4 Measurement of the Number of Surviving Bacteria

The agar plate pouring technique was carried out with reference to New GMP Microbial Testing Methods 1) and Standard Methods of Analysis in Food Safety Regulation 2).

[1] 500 µL of the sample for bacterial counting was collected, and 10-fold dilution series from $10^1$-fold to $10^6$-fold were made using 4.5 mL of a diluent solution.

[2] 1 mL each of the undiluted sample for bacterial counting and the diluted bacterial suspensions was dispensed to each sterile dish.

[3] 15 mL of a measurement medium (TSA+) incubated in a thermostat bath set to approximately 47° C. was rapidly dispensed to the dish.

[4] After solidification of the measurement medium, the resulting pour plates were inverted in an incubator, and cultured at 35° C. until colonies became able to be counted (approximately 2 days).

[5] After the culture, colonies that proliferated in the pour plates were visually counted. A pour plate in which the number of colonies was too many to distinguish the colonies was regarded as TNTC (too numerous to count) without counting.

[6] The number of colonies was multiplied by the dilution ratio to calculate the number of surviving bacteria.

2-4 Results

The results are shown in FIG. 5 and Table 2.

TABLE 2

The number of surviving bacteria in hamster oral cavity

| Test material | n | The number of surviving bacteria {Mean ± SD[$Log_{10}$(CFU/swab)]} | | | |
|---|---|---|---|---|---|
| | | Baseline | 0 hr | 8 hrs | 24 hrs |
| Base | 4 | 6.09 ± 0.87 | 5.26 ± 0.50 | 5.55 ± 0.52 | 5.86 ± 0.53 |
| 0.1% OPB-1 | 4 | 6.13 ± 0.40 | 3.13 ± 0.52 | 3.98 ± 1.03 | 5.57 ± 0.69 |
| 0.1% OPB-2 | 4 | 6.16 ± 0.27 | 3.24 ± 0.34 | 4.52 ± 0.65 | 6.24 ± 0.22 |
| Peridex | 4 | 6.17 ± 0.65 | 4.04 ± 0.69 | 3.86 ± 0.92 | 5.68 ± 0.49 |
| 0.47% PVP-I | 4 | 6.50 ± 0.39 | 4.35 ± 0.33 | 5.79 ± 0.31 | 6.08 ± 0.47 |

The number of bacteria in the oral cavity before test material administration did not differ among the groups. The bactericidal efficacy was 0.1% OPB-1=0.1% OPB-2>0.12% CHG>0.47% PVP-I>Base immediately after test material administration, was 0.1% OPB-1=0.1% OPB-2=0.12% CHG>0.47% PVP-I=Base 8 hours after administration, and did not differ among the groups 24 hours after administration. From these results, the bactericidal efficacy in the oral cavity was equivalent between 0.1% OPB and 0.12% CHG, and 0.47% PVP-I had a weak immediate effect with no persistent activity observed.

The reason why the bactericidal activity of 0.47% PVP-I was low in this test was that inactivation by proteins and the like in the oral cavity probably made a significant contribution thereto. 0.12% CHG, as in 0.1% OPB, was considered as a bactericidal antiseptic having persistent activity in the oral cavity.

Example 3

3. Bactericidal Test in Oral Cavity Using Hamster—2

This test was aimed at studying the influence of an olanexidine concentration on the bactericidal efficacy of a gargle (bactericidal antiseptic) on the mucosa in the oral cavity of normal hamsters.

3-1 Test Material

Test substances and a control substance were collectively used as test materials.

3-1-1 Test Substance 1
Designation: 0.1% OPB-1
Formula: olanexidine gluconate . . . 0.10 w/v %
  polyoxyethylene (20) polyoxypropylene (20) glycol . . . 0.07 w/v %
  polyoxyethylene (160) polyoxypropylene (30) glycol . . . 0.10 w/v %

3-1-2 Test substance 2
Designation: 0.1% OPB-2
Formula: olanexidine gluconate . . . 0.10 w/v %
  polyoxyethylene (20) polyoxypropylene (20) glycol . . . 0.07 w/v %
  polyoxyethylene (160) polyoxypropylene (30) . . . 1.00 w/v %

3-1-3 Test Substance 3
Designation: 0.5% OPB-3
Formula: olanexidine gluconate . . . 0.50 w/v %
  polyoxyethylene (20) polyoxypropylene (20) . . . 0.36 w/v %
  polyoxyethylene (160) polyoxypropylene (30) . . . 5.00 w/v %

3-1-4 Test Substance 4
Designation: 1% OPB-2
Formula: olanexidine gluconate . . . 1.00 w/v %
  polyoxyethylene (20) polyoxypropylene (20) glycol . . . 0.72 w/v %
  polyoxyethylene (160) polyoxypropylene (30) glycol . . . 10.00 w/v %

3-1-5 Control Substance
Designation: base
Formula: polyoxyethylene (20) polyoxypropylene (20) glycol . . . 0.07 w/v %
  polyoxyethylene (160) polyoxypropylene (30) glycol . . . 0.10 w/v %

3-2 Animal Used
Male Slc: Syrian hamsters which were 6 weeks old upon receipt were used to conduct a test on 3 animals per group.

3-3 Testing Method 3-3-1 Anesthesia
Gas anesthesia [induction of anesthesia: 3.0 L/min of air with 3% isoflurane (manufactured by Mylan Seiyaku Ltd.), the concentration of continuous anesthesia was appropriately adjusted] was carried out.

3-3-2 Test Material Administration
Each hamster was fixed in the supine position under anesthesia, and 1 mL of each test material was injected to one cheek pouch. One minute later, the test material was eliminated, and a redundant test material was drawn out of the cheek pouch using a sterile swab.

3-3-3 Bacterial Collection
Bacteria were collected from both the cheek pouches under anesthesia using a sterile swab at a total of 5 time points (before test material administration, 0 hr, 1 hr, 3 hr, and 6 hr). The swab after the collection was dipped in 5 mL of a SCDLP medium, then stirred, and used as a sample for bacterial counting.

3-3-4 Measurement of the Number of Surviving Bacteria
The number of surviving bacteria was measured in the same way as in 2-3-4.

3-4 Results
The results are shown in FIG. 6. As is evident from the results, 0.1% OPB can reduce the number of bacteria to a low value persistently (up to 6 hours later). The persistent activity was better at an OPB concentration of 0.5 w/v % or higher.

Example 4

4. Oral Mucosal Irritancy Test Using Hamster—1

In this test, study drug formulations with varying base formulas of 0.1% olanexidine gluconate were repeatedly administered to the cheek pouches of hamsters for 14 days, and comparatively studied for the degree of irritancy.

4-1 Test Substance
4-1-1 Test substance 1
Designation: 0.1% OPB-1
Formula: olanexidine gluconate . . . 0.10 w/v %
  Pluronic L-44 . . . 0.07 w/v %

4-1-2 Test Substance 2
Designation: 0.1% OPB-2
Formula: olanexidine gluconate . . . 0.10 w/v %
  Pluronic L-44 . . . 0.07 w/v %
  Pluronic L-31 . . . 1.0 w/v %

4-1-3 Test Substance 3
Designation: 0.1% OPB-3
Formula: olanexidine gluconate . . . 0.10 w/v %
  Pluronic L-44 . . . 0.07 w/v %
  Pluronic P-123 . . . 1.0 w/v %

4-1-4 Test Substance 4
Designation: 0.1% OPB-4
Formula: olanexidine gluconate . . . 0.10 w/v %
  Pluronic L-44 . . . 0.07 w/v %
  Pluronic P-85 . . . 1.0 w/v %

4-1-5 Test Substance 5
Designation: 0.1% OPB-5
Formula: olanexidine gluconate . . . 0.10 w/v %
  Pluronic L-44 . . . 0.07 w/v %
  Pluronic F-127 . . . 1.0 w/v %

4-1-6 Test Substance 6
Designation: 0.1% OPB-6
Formula: olanexidine gluconate . . . 0.10 w/v %
  Pluronic L-44 . . . 0.14 w/v %
  Pluronic F-68 . . . 1.0 w/v %

4-1-7 Test substance 7
Designation: 0.1% OPB-7
Formula: olanexidine gluconate . . . 0.10 w/v %

Pluronic L-44 . . . 0.07 w/v %
Trehalose . . . 5.0 w/v %

4-2 Animal Used

Male Slc: Syrian hamsters which were 8 weeks old upon receipt were used to conduct a test on 3 animals per group.

4-3 Testing Method 4-3-1 Test Substance Application Method (1) Amount Applied 1 mL of each test substance was applied to the right cheek pouch.

(2) Application Method

[1] Anesthesia was induced by gas anesthesia [induction of anesthesia: 3.0 L/min of air with 3% isoflurane (manufactured by Mylan Seiyaku Ltd.)].

[2] Each animal was fixed in the supine position under maintenance of anesthesia (the concentration was appropriately adjusted). The cheek pouch of the animal was pulled using a swab, and the pulled cheek pouch was lightly pinched with one hand.

[3] Foreign matter such as feed attached to the mucosa of the cheek pouch was removed using saline and a swab for good hygiene. Then, the cheek pouch was put back in place.

[4] 1 mL of each test substance was applied to the right cheek pouch using a 1 mL syringe and a probe for oral administration, and a vacant probe for oral administration fitted into a 1 mL syringe was inserted to the left cheek pouch, and decannulated.

[5] Thirty seconds after application, the animal was reversed to the prone position so as to prevent the backflow of the test substance into the respiratory tract, and the test substance was eliminated. The whole redundant test substance in the oral cavity was removed using a swab.

[6] The color tone and the like of the cheek mucosa at the application site were observed and recorded. A collar for hamsters was worn on the neck of the animal, and the animal was then brought back to a cage.

[7] The manipulation described above was repeated twice a day (morning and evening) for 14 days.

4-3-2 Examination and Observation (1) Observation of General Status

The general status was observed as to all the animals of each group before application of the test material and at the completion of application in the application period (Day 1 to Day 14). The observation was also performed on the day following the end of the application period (Day 15).

(2) Body Weight Measurement

The body weight was measured as to all the animals of each group before application of the test material in the application period (Day 1 to Day 14). The measurement was also performed on the day following the end of the application period (Day 15). However, the body weight was not measured on Days 13 and 14 due to the breakdown of a body weight scale.

(3) Macroscopic Observation Method at Application Site

The status of the mucosa of the cheek pouch was observed and scored as to the cheek pouches of all the animals of each group before application of the test material and at the completion of application in the application period (Day 1 to Day 14). The observation was also performed on the day (24±2 hours) following the end of the application period (Day 15). The observation site was set to the cheek mucosa at a site contacted with each test material. As for the evaluation technique of macroscopic observation, the degrees of erythema and eschar formation were numerically graded (stomatitis grade) according to the observation criteria and the numerical grading described in Table 3 below (ISO 10993-10, Annex B.3 "Table B.2 Grading system for oral and penile reactions"). Other detected manifestations were also recorded. On the basis of the obtained observation results, the respective numerical grades for the mucosa of the animals of each group were added for each test material, and the sum was divided by the number of observations and the number of animals to determine an average value (rounded to unit), which was used as a reference material for comprehensive evaluation.

TABLE 3

Table B.2 Grading system for oral and penile reactions

| (Erythema and eschar formation) | Numerical grading |
|---|---|
| No erythema | 0 |
| Very slight erythema (barely perceptible) | 1 |
| Well-defined erythema | 2 |
| Moderate erythema | 3 |
| Severe erythema (beet-redness) to eschar formation preventing grading of erythema | 4 |

(4) Pathological Examination

Each animal was sacrificed by blood-letting under isoflurane anesthesia after the completion of macroscopic observation on the day following the end of the application period, and the right and left cheek pouches were collected and fixed in a 10% neutral buffered formalin solution. HE-stained specimens were made according to a routine technique, and pathological examination was carried out. As for the evaluation technique of macroscopic observation, manifestations or grades were recorded as to each item of epithelium, leukocyte infiltration, hyperemia and edema according to the criteria described in ISO 10993-10, Annex B.3 "Table B.3 Grading system for microscopic examination for oral, penile, rectal and vaginal tissue reaction". Other observed manifestations were also recorded.

(5) Comprehensive Evaluation

The influence of each test material on the oral mucosa was comprehensively evaluated on the basis of the degree of reaction of each test material obtained from the macroscopic observation results and the pathological observation results about the cheek mucosa, with reference to transitions in general status and body weight in the observation period.

4-4 Results 4-4-1 General Status

No abnormality was observed in any of the animals.

4-4-2 Body Weight

The results are shown in FIG. 7. The body weight of the 0.1% OPB-5 group was hardly changed. The average values of the other groups were gradually increased.

4-4-3 Macroscopic Observation of Application Site

Figure 8:
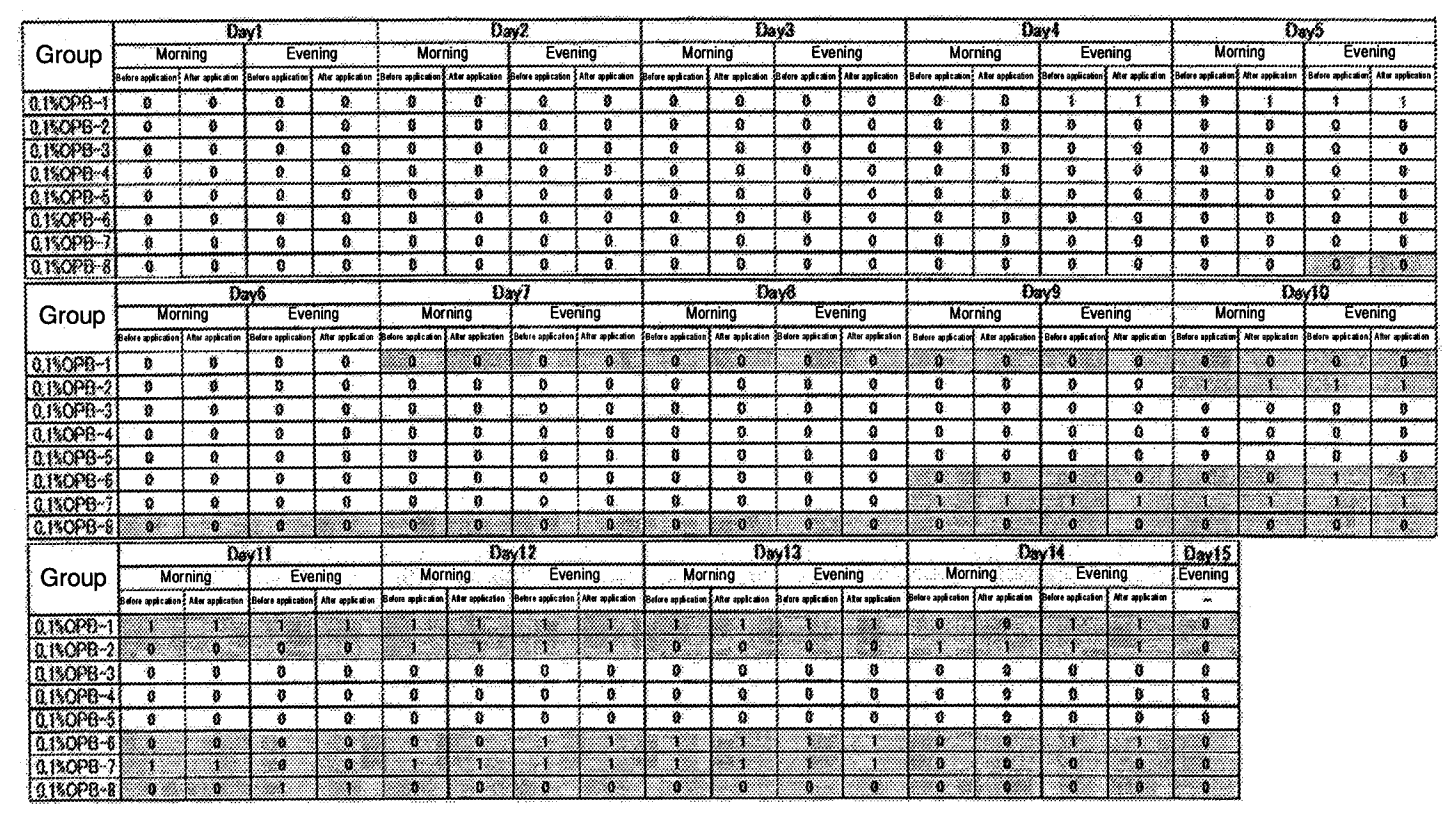

The results are shown in FIG. 8, and the cheek pouch of each group on the final day is shown in Photos 1 to 8 of FIG. 9. Irritancy such as erythema was hardly observed in all the drug formulations. However, a leukoplakia-like symptom (increased keratosis or thickening) was observed in 0.1% OPB-1, -2, -6, -7 and -8. On the other hand, no abnormality was observed in 0.1% OPB-3, -4 and -5.

4-4-4 Histopathological Examination

The results are shown in FIG. 10. An average inflammation index of each individual and an average inflammation index of each group were calculated by grading of epithelium (cell degeneration, metaplasia and erosion), leukocyte infiltration, hyperemia and edema according to the evaluation criteria described in ISO 10993-10, Annex B.3 "Table B.3 Grading system for microscopic examination for oral, penile, rectal and vaginal tissue reaction". Manifestations other than the evaluation criteria were also recorded. As a result, no change was observed in the average value of the 0.1% OPB-3 group. Cell degeneration of the epithelium and minimum to moderate leukocyte infiltration were observed in the other groups including the 0.1% OPB-1 group, and the inflammation index was evaluated as being the minimum of 1 to 3. In these groups, very slight intercellular edema and very slight to slight hyperkeratosis were observed as manifestations other than the evaluation criteria.

These results suggested that the base Pluronic P-123 used for 0.1% OPB-3 is particularly useful as a base for a drug formulation for application of olanexidine gluconate to the oral mucosa. The results also suggested that Pluronic P-85 and Pluronic F-127 used for 0.1% OPB-4 and -5, which were found to be free from abnormality in macroscopic observation, were also usable as bases for a drug formulation for application of olanexidine gluconate to the oral mucosa.

Example 5

5. Oral Mucosal Irritancy Test Using Hamster—2

The irritancy test of Example 4 suggested that the base Pluronic P-123 is useful as a base for a drug formulation for application of olanexidine gluconate to the oral mucosa. Accordingly, in this test, Pluronic P-123 was adopted as a base for making a drug formulation having no irritation, and subsequently, an OPB concentration and a base concentration were studied. The test system was carried out by performing repeated administration to the hamster cheek pouch, and prolonging the period from 2 weeks to 4 weeks.

5-1 Test Substance
5-1-1 Test Substance 1
Designation: 0.1% OPB-1
Formula: olanexidine gluconate . . . 0.10 w/v %
    Pluronic L-44 . . . 0.07 w/v %
    Pluronic P-123 . . . 0.50 w/v %
5-1-2 Test Substance 2
Designation: 0.1% OPB-2
Formula: olanexidine gluconate . . . 0.10 w/v %
    Pluronic L-44 . . . 0.07 w/v %
    Pluronic P-123 . . . 1.0 w/v %
5-1-3 Test Substance 3
Designation: 0.1% OPB-3
Formula: olanexidine gluconate . . . 0.10 w/v %
    Pluronic L-44 . . . 0.07 w/v %
    Pluronic P-123 . . . 0.50 w/v %
    Lipidure® . . . 1.0 w/v %
5-1-4 Test Substance 4
Designation: 0.1% OPB-4
Formula: olanexidine gluconate . . . 0.10 w/v %
    Pluronic L-44 . . . 0.07 w/v %
    Pluronic P-123 . . . 1.0 w/v %
    Lipidure® . . . 1.0 w/v %
5-1-5 Test Substance 5
Designation: 0.3% OPB-1
Formula: olanexidine gluconate . . . 0.30 w/v %
    Pluronic L-44 . . . 0.22 w/v %
    Pluronic P-123 . . . 1.50 w/v %
5-1-6 Test Substance 6
Designation: 0.3% OPB-2
Formula: olanexidine gluconate . . . 0.30 w/v %
    Pluronic L-44 . . . 0.22 w/v %
    Pluronic P-123 . . . 3.0 w/v %
5-1-7 Test Substance 7
Designation: 0.3% OPB-3
Formula: olanexidine gluconate . . . 0.30 w/v %
    Pluronic L-44 . . . 0.22 w/v %
    Pluronic P-85 . . . 1.50 w/v %
5-1-8 Test Substance 8
Designation: 0.3% OPB-4
Formula: olanexidine gluconate . . . 0.30 w/v %
    Pluronic L-44 . . . 0.22 w/v %
    Pluronic P-85 . . . 3.0 w/v %
5-1-9 Test Substance 9
Designation: 0.5% OPB-1
Formula: olanexidine gluconate . . . 0.50 w/v %
    Pluronic L-44 . . . 0.36 w/v %
    Pluronic P-123 . . . 2.50 w/v %
5-1-10 Test Substance 10
Designation: 0.5% OPB-2
Formula: olanexidine gluconate . . . 0.50 w/v %
    Pluronic L-44 . . . 0.36 w/v %
    Pluronic P-123 . . . 5.0 w/v %
5-1-11 Test Substance 11
Designation: 0.5% OPB-3
Formula: olanexidine gluconate . . . 0.50 w/v %
    Pluronic L-44 . . . 0.36 w/v %
    Pluronic P-123 . . . 2.50 w/v % Lipidure® . . . 1.0 w/v %
5-1-12 Test Substance 12
Designation: 0.5% OPB-4
Formula: olanexidine gluconate . . . 0.50 w/v %
    Pluronic L-44 . . . 0.36 w/v %
    Pluronic P-123 . . . 5.0 w/v %
    Lipidure® . . . 1.0 w/v %
5-2 Animal Used Male Slc: Syrian hamsters which were 8 weeks old upon receipt were used to conduct a test on 3 animals per group.

5-3 Testing Method
5-3-1 Test Substance Application Method
(1) Amount Applied 1 mL of each test substance was applied to the left cheek pouch.

(2) Application Method

[1] Anesthesia was induced by gas anesthesia [induction of anesthesia: 3.0 L/min of air with 3% isoflurane (manufactured by Mylan Seiyaku Ltd.)].

[2] Each animal was fixed in the supine position under maintenance of anesthesia (the concentration was appropriately adjusted). The cheek pouch of the animal was pulled using a swab, and the pulled cheek pouch was lightly pinched with one hand.

[3] Foreign matter such as feed attached to the mucosa of the cheek pouch was removed using saline and a swab for good hygiene. Then, the cheek pouch was put back in place.

[4] 1 mL of each test substance was applied to the left cheek pouch using a 1 mL syringe and a probe for oral administration, and a vacant probe for oral administration fitted into a 1 mL syringe was inserted to the right cheek pouch, and decannulated.

[5] Thirty seconds after application, the animal was reversed to the prone position so as to prevent the backflow of the test substance into the respiratory tract, and the test substance was eliminated. The whole redundant test substance in the oral cavity was removed using a swab.

[6] The color tone and the like of the cheek mucosa at the application site were observed and recorded, and the animal was then brought back to a cage.

[7] The manipulation described above was repeated twice a day (morning and evening) for 28 days.

5-3-2 Examination and Observation
(1) Observation of General Status

The general status was observed as to all the animals of each group before application of the test material and at the completion of application in the application period (Day 1 to Day 28). The observation was also performed on the day following the end of the application period (Day 29).

(2) Body Weight Measurement

The body weight was measured as to all the animals of each group before application of the test material in the application period (Day 1 to Day 28). The measurement was also performed on the day following the end of the application period (Day 29).

(3) Macroscopic Observation Method at Application Site

The status of the mucosa of the cheek pouch was observed and scored as to the cheek pouches of all the animals of each group before application of the test material in the application period (Day 1 to Day 28). The observation was also performed on the day (24±2 hours) following the end of the application period (Day 29). The observation site was set to the cheek mucosa at a site contacted with each test material. As for the evaluation technique of macroscopic observation, the degrees of erythema and eschar formation were numerically graded (stomatitis grade) according to the observation criteria and the numerical grading described in Table 3 above (ISO 10993-10, Annex B.3 "Table B.2 Grading system for oral and penile reactions"). Other detected manifestations were also recorded. On the basis of the obtained observation results, the respective numerical grades for the mucosa of the animals of each group were added for each test material, and the sum was divided by the number of observations and the number of animals to determine an average value (rounded to unit), which was used as a reference material for comprehensive evaluation.

(4) Pathological Examination

Each animal was sacrificed by blood-letting under isoflurane anesthesia after the completion of macroscopic observation on the day following the end of the application period, and the right and left cheek pouches were collected and fixed in a 10% neutral buffered formalin solution. HE-stained specimens were made according to a routine technique, and pathological examination was carried out. As for the evaluation technique of macroscopic observation, manifestations or grades were recorded as to each item of epithelium, leukocyte infiltration, hyperemia and edema according to the criteria described in ISO 10993-10, Annex B.3 "Table B.3 Grading system for microscopic examination for oral, penile, rectal and vaginal tissue reaction". Other observed manifestations were also recorded.

(5) Comprehensive Evaluation

The influence of each test material on the oral mucosa was comprehensively evaluated on the basis of the degree of reaction of each test material obtained from the macroscopic observation results and the pathological observation results about the cheek mucosa, with reference to transitions in general status and body weight in the observation period.

5-4 Results 5-4-1 General Status

No abnormality was observed in any of the animals.

5-4-2 Body Weight

The body weight was increased over time in all the groups, and hardly differed among the groups.

5-4-3 Macroscopic Observation of Application Site

Figure 11:
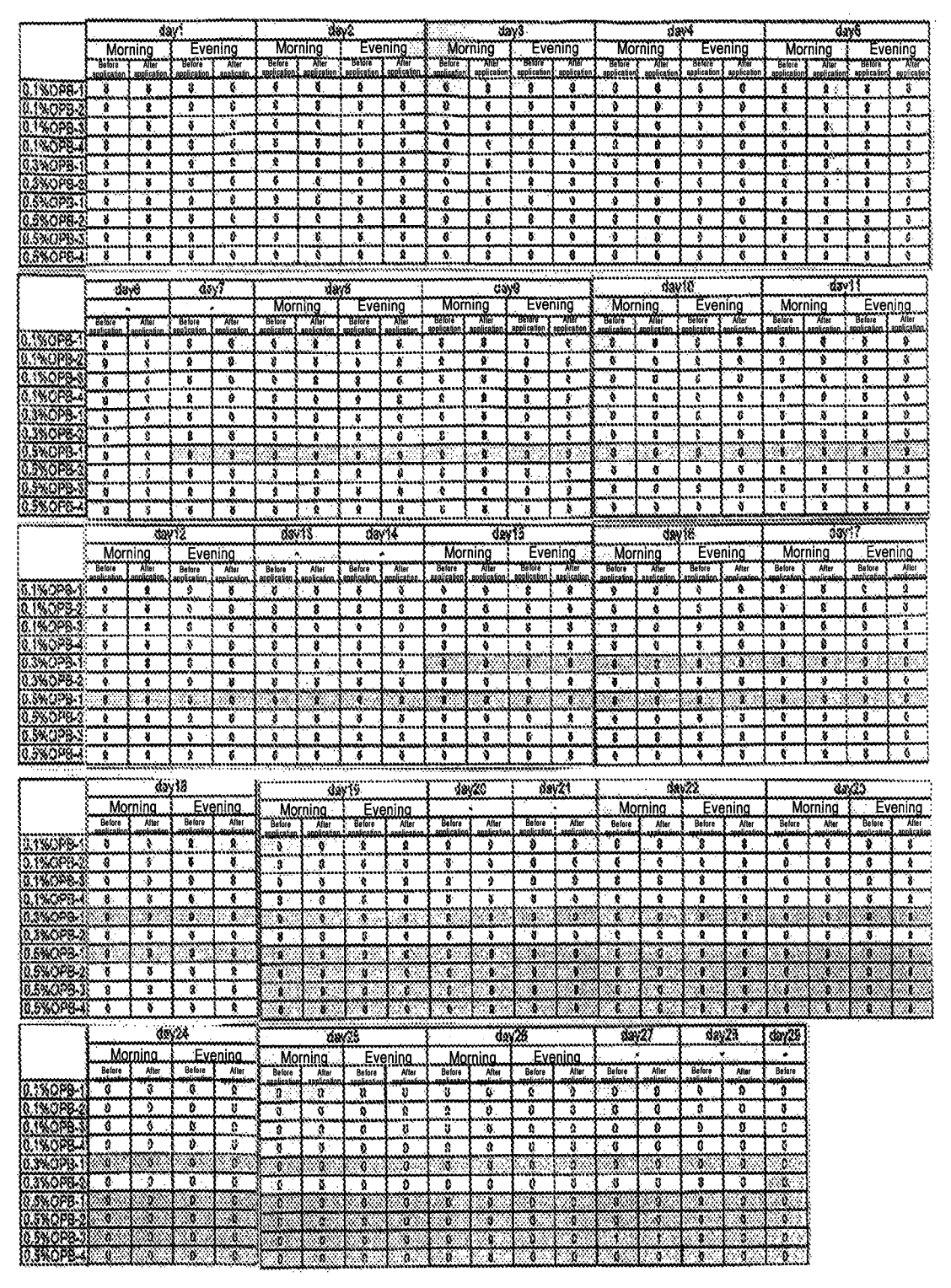

The results are shown in FIG. 11. Irritancy such as erythema was not observed in all the drug formulations (numerical grading: 0). However, a leukoplakia-like symptom (increased keratosis or thickening) was observed in OPB having a concentration of 0.3% or higher. On the other hand, no abnormality was observed in OPB having a concentration of 0.1%.

5-4-4 Histopathological Examination

The results are shown in FIG. 12. An average inflammation index of each individual and an average inflammation index of each group were calculated by grading of epithelium (cell degeneration, metaplasia and erosion), leukocyte infiltration, hyperemia and edema according to the evaluation criteria described in ISO 10993-10, Annex B.3 "Table B.3 Grading system for microscopic examination for oral, penile, rectal and vaginal tissue reaction". Manifestations other than the evaluation criteria were also recorded. As a result, no inflammatory reaction was observed in each group of 0.1% OPB. Degeneration of the epithelium and leukocyte infiltration were observed in each group of OPB having a concentration of 0.3% or higher, and all the reactions were minimal with an inflammation index of 1 to 3. Very slight to slight hyperkeratosis was observed as manifestations other than the evaluation criteria in some individuals of the 0.1% OPB group, and very slight to moderate hyperkeratosis and very slight outgrowth of prickle cells were observed in each group of OPB having a concentration of 0.3% or higher. In addition, intraepidermal microabscess observed in the control group (right cheek pouch: Sham-ope side) seemed to be a naturally occurring lesion.

Example 6

6. Efficacy Test in 5-FU-Induced Hamster Stomatitis Model—1

In this test, the efficacy of an OPB drug formulation was tested in 5-FU-induced stomatitis models. Specifically, measurements of the number of bacteria in the oral cavity over time and stomatitis evaluation were performed by gargling in the oral cavity with 0.1% OPB in 5-FU-induced stomatitis models.

6-1 Test Material

A test substance and a control substance were collectively used as test materials.

6-1-1 Test Substance

Designation: 0.1% OPB

Formula: olanexidine gluconate . . . 0.10 w/v % polyoxyethylene (20) polyoxypropylene (20) glycol . . . 0.14 w/v % polyoxyethylene (160) polyoxypropylene (30) glycol . . . 0.10 w/v %

6-1-2 Control Substance

Designation: base

Formula: polyoxyethylene (20) polyoxypropylene (20) glycol . . . 0.07 w/v % polyoxyethylene (160) polyoxypropylene (30) glycol . . . 0.10 w/v %

6-2 Animal Used

Male Slc: Syrian hamsters which were 6 weeks old upon receipt were used to conduct a test on 5 animals per group.

6-3 Testing Method 6-3-1 Anesthesia

Gas anesthesia [induction of anesthesia: 3.0 L/min of air with 3% isoflurane (manufactured by Mylan Seiyaku Ltd.), the concentration of continuous anesthesia was appropriately adjusted] was carried out.

6-3-2 Stomatitis Model Making

5-FU was intraperitoneally administered at 60 mg/kg to the hamsters under anesthesia. The administration was performed a total of twice on Day 0 and Day 2.

On Day 4, the cheek pouch was pulled out from each hamster under anesthesia. Feed and floor mat for laboratory animals accumulated in the cheek pouch were removed, and the cheek pouch was patted with a cotton pad saturated with saline. The surface layer (horny layer) of the cheek pouch was brushed with a precision wire brush (φ2.34 mm, manufactured by Sumflex. Co., Ltd.). The cheek pouch thus brushed was brought back to the oral cavity.

6-3-3 Test Material Administration

Each hamster was fixed in the supine position under anesthesia, and 1 mL of each test material was injected to one cheek pouch. Thirty seconds later, the test material was eliminated, and a redundant test material was drawn out of the cheek pouch using a sterile swab. This administration by the gargling manipulation was performed twice a day. The administration was not carried out after the disorder of stomatitis reached the peak.

6-3-4 Bacterial Collection

On Days 0, 4, 7, 10, and 17, bacteria were collected from both the cheek pouches under anesthesia using a sterile swab at a total of 4 time points (before the first test material administration, 0 hr, and 6 hr later). However, on days 10 and 17 without test material application, bacteria were collected only once. The swab after the collection was dipped in 5 mL of a SCDLP medium, then stirred, and used as a sample for bacterial counting.

6-3-5 Measurement of the Number of Surviving Bacteria

The agar plate pouring technique was carried out with reference to New GMP Microbial Testing Methods 1) and Standard Methods of Analysis in Food Safety Regulation 2).

[1] 500 μL of the sample for bacterial counting was collected, and 10-fold dilution series from $10^1$-fold to $10^4$-fold were made using 4.5 mL of a diluent solution.

[2] 1 mL each of the undiluted sample for bacterial counting and the diluted bacterial suspensions was dispensed to each sterile dish.

[3] 15 mL of a measurement medium (TSA+) incubated in a thermostat bath set to approximately 47° C. was rapidly dispensed to the dish.

[4] After solidification of the measurement medium, the resulting pour plates were inverted in an incubator, and cultured at 35° C. until colonies became able to be counted (approximately 2 days).

[5] After the culture, colonies that proliferated in the pour plates were visually counted. A pour plate in which the number of colonies was too many to distinguish the colonies was regarded as TNTC (too numerous to count) without counting.

6-3-6 Calculation of the Number of Surviving Bacteria

The number of colonies adopted on the basis of the section 6-3-5 was divided by the dilution ratio to determine the number of surviving bacteria (CFU/mL). The number of colonies adopted was rounded off to one decimal place and displayed. The number of surviving bacteria (CFU/swab) was calculated according to the following expression.

A: the number of colonies adopted $$\text{The number of surviving bacteria (CFU/swab)} = A \times \text{Dilution ratio} \times \text{Amount of the sample fluid (5 mL)}$$

Log reduction was further determined according to the expression given below from the logarithmic value of the number of surviving bacteria. The log reduction was rounded off to two decimal places and displayed. When the number of surviving bacteria was 1 or less, the logarithmic value was set to 0.

B: logarithmic value of the number of viable bacteria at the baseline

C: logarithmic value of the number of viable bacteria after test material embrocation $$\text{Log reduction} = B - C$$

6-3-7 Statistical Analysis

A mean and standard deviation were determined on the number of viable bacteria (CFU/swab) of each group and its logarithmic value. The number of viable bacteria was rounded to unit and displayed in integer. The logarithmic value of the number of viable bacteria was rounded off to two decimal places and displayed. When the number of viable bacteria was 0, the logarithmic value of the number of viable bacteria was set to 0. No assay was conducted because of an exploratory test.

6-3-8 Stomatitis Evaluation

A stomatitis grade was evaluated on the basis of Table 4 below.

TABLE 4

| Grade | Status |
|---|---|
| 0 | Neither erythema nor vasodilation |
| 1 | Erythema and vasodilation |
| 2 | Serious erythema attended with superficial mucosal erosion |
| 3 | Mucosal ulceration (25%) |
| 4 | Mucosal ulceration (50%) |
| 5 | Mucosal ulceration (100%) |

6-4 Results 6-4-1 the Number of Bacteria

The results are shown in Table 5 and FIG. 13. Decrease in the number of bacteria after administration was marked in the 0.1% OPB group on Days 0, 4, and 10, whereas the value of the decreased number of bacteria was very small on Day 7 when increase in severity of stomatitis was marked.

TABLE 5

The number of surviving bacteria in hamster oral cavity

The number of surviving bacteria {Mean ± SD [$Log_{10}$ (CFU/swab)]}

| Test material | n | 0 day | | | 4 day | | | 7 day | | | 10 day | | | 17 day |
|---|---|---|---|---|---|---|---|---|---|---|---|---|---|---|
| | | pre | 0 h | 6 h | pre | 0 h | 6 h | pre | 0 h | 6 h | Pre | 0 h | 6 h | pre |
| No procedure | 5 | 6.78 ± 0.43 | 6.72 ± 0.38 | 6.79 ± 0.22 | 7.07 ± 0.49 | 6.97 ± 0.53 | 6.82 ± 0.20 | 7.03 ± 0.48 | 6.84 ± 0.35 | 6.90 ± 0.21 | 6.59 ± 0.26 | 6.54 ± 0.30 | 6.54 ± 0.18 | 6.65 ± 0.16 |
| Base | 5 | 6.61 ± 0.52 | 5.95 ± 0.39 | 6.10± 0.39 | 6.62 ± 0.42 | 6.08 ± 0.09 | 6.30 ± 0.20 | 7.12 ± 0.07 | 6.89 ± 0.29 | 6.68 ± 0.23 | 6.61 ± 0.59 | 6.67 ± 0.57 | 6.85 ± 0.31 | 6.68 ± 0.56 |
| 0.1% OPB | 5 | 6.86 ± 0.42 | 4.69 ± 0.15 | 4.78 ± 0.68 | 6.78 ± 0.30 | 5.32 ± 0.25 | 6.31 ± 0.55 | 7.02 ± 0.19 | 6.36 ± 0.44 | 6.84 ± 0.35 | 6.60 ± 0.35 | 5.82 ± 0.27 | 6.54 ± 0.32 | 6.50 ± 0.27 |

6-4-2 Stomatitis Grade

The results are shown in FIG. 14. The stomatitis grade was markedly low in the 0.1% OPB group.

In this test, the value of the decreased number of bacteria was low on Day 7 in the 0.1% OPB group probably because of reduction in bactericidal activity due to the bacterial collection method or an excess of an effusion. This test suggested that increase in severity of stomatitis is mitigated by administering 0.1% OPB and thereby keeping the oral cavity clean.

Example 7

7. Efficacy Test in 5-FU-Induced Hamster Stomatitis Model—2

In this test, the stomatitis-mitigating effects of 0.1% olanexidine gluconate and 0.1% CHG were comparatively studied in 5-FU-induced hamster stomatitis models.

7-1 Test Material

Test substances and a control substance were collectively used as test materials.

7-1-1 Test Substance 1

Designation: 0.1% OPB

Formula: olanexidine gluconate . . . 0.10 w/v %
Pluronic L-44 . . . 0.07 w/v %

7-1-2 Test Substance 2

Designation: Peridex®/0.1% CHG

Manufacturer: 3M ESPE Dental Products

Formula: chlorhexidine gluconate . . . 0.12 w/v %

7-1-3 Control substance

Designation: base

Formula: polyoxyethylene (20) polyoxypropylene (20) glycol . . . 0.07 w/v %

7-2 Bacterium Used

In this test, *Staphylococcus aureus* (ATCC No: 6538, manufactured by Microbiologics, Inc.) was used, which is a normal inhabitant in the oral cavity.

7-3 Animal Used

Male Slc: Syrian hamsters which were 6 weeks old upon receipt were used to conduct a test on 5 animals per group.

7-4 Testing Method 7-4-1 Preparation of Test Bacterial Suspension

[1] A stored vial containing bacterial pellets was taken out and brought back to room temperature.

[2] One bacterial pellet was taken out of the vial and transferred to a sterile tube.

[3] 0.5 mL of saline was added thereto.

[4] The bacterial pellet was squashed with a sterile swab to prepare a suspended bacterial fluid.

[5] The suspended bacterial fluid was inoculated to a round area of approximately 2 cm in diameter in a TSA plate using a sterile swab, and streaked from the inoculation area using a platinum loop.

[6] The streaked TSA plate was inverted, and cultured until colonies were formed.

[7] A single colony was selected from among the formed colonies, collected with a platinum needle, and stabbed to a Casitone medium.

[8] The Casitone medium in which the inoculant was stabbed was cultured until proliferation of bacteria became able to be confirmed.

[9] After confirmation of the proliferation of bacteria, the bacteria were refrigerated (set value: 2 to 8° C.).

[10] A portion of the test bacteria refrigerated in the Casitone medium was collected with a platinum needle, transferred to a 14 mL sterile tube containing 5 mL of an MHB medium, and static cultured until the bacteria proliferated.

[11] After the culture, 10 μL of the culture solution was collected with a sterile tip, transferred again to a 14 mL sterile tube containing 5 mL of an MHB medium, and static cultured until the bacteria proliferated.

[12] After the culture, approximately 5 mL of the test bacterial culture solution subcultured in the MHB medium was recovered into a 15 mL conical tube. After addition of 8 mL of saline, the mixture was gently stirred.

[13] The tube was centrifuged at 3000 rpm at 23° C. for 10 minutes (cooled centrifuge 5800, rotor RS-720, manufactured by Kubota Corp.), and the supernatant was discarded.

[14] The precipitated test bacteria were suspended by the addition of 1 mL of distilled water (Otsuka Distilled Water, manufactured by Otsuka Pharmaceutical Factory, Inc.).

[15] The suspended bacterial fluid was transferred to a 14 mL sterile tube, and the turbidity was determined using McFarland Standard (product No. 70900, manufactured by Sysmex-Biomerieux Co., Ltd."). The concentration of the bacterial suspension was adjusted by the addition of saline so as to attain McFarland 5.

[16] The suspended bacterial fluid adjusted to McFarland 5 was used as a test bacterial suspension.

7-4-2 Anesthesia

Gas anesthesia [induction of anesthesia: 3.0 L/min of air with 3% isoflurane (Mylan Seiyaku Ltd.), the concentration of continuous anesthesia was appropriately adjusted] was carried out.

7-4-3 Stomatitis Model Making

5-FU was intraperitoneally administered at 60 mg/kg to the hamsters under anesthesia. The administration was performed a total of twice on Day 0 and Day 2. On Day 4, the cheek pouch was pulled out from each hamster under anesthesia. Feed and floor mat for laboratory animals accumulated in the cheek pouch were removed, and the cheek pouch was patted with a cotton pad saturated with saline. The surface layer (horny layer) of the cheek pouch was brushed with a precision wire brush (φ2.34 mm, manufactured by Sumflex. Co., Ltd.). The cheek pouch thus brushed was brought back to the oral cavity.

7-4-4 Test Material Administration

Each test material was embrocated twice a day to the hamster cheek pouch under anesthesia using a swab (for 4 days from the grouping day). However, on the 4th day, the administration was performed once (only in the morning).

7-4-5 Test Bacterial Suspension Embrocation

The test bacterial suspension prepared in 7-4-1 was embrocated once a day before the test material administration in the morning to the hamster cheek pouch under anesthesia using a platinum loop (for 5 days from the grouping day).

7-4-6 Stomatitis Evaluation

A stomatitis grade was evaluated on the basis of Table 4 above.

7-4-7 Statistical Analysis

A mean and standard deviation were determined on the grade of each group, and a graph was created using only the mean. No assay was conducted because of exploratory analysis.

7-5 Results

The results are shown in FIG. 15. A tendency to mitigate increase in severity of stomatitis was seen in the 0.1% OPB group compared with the base and 0.1% CHG groups. The grade was almost the same with no difference between the base group and the 0.1% CHG group. From the effect of mitigating increase in severity of stomatitis, the 0.1% OPB was considered to be superior in bactericidal efficacy on the embrocated bacteria or the normal inhabitant in the mucosa of the cheek pouch to 0.1% CHG.

Example 8

8. Efficacy test in hamster model of stomatitis induced by using 5-FU and radiation irradiation in combination In this test, a drug formulation of 0.1% OPB containing Pluronic P-123 as a base was applied by the gargling technique to hamster models of stomatitis induced by using 5-FU and radiation irradiation in combination, and comparatively studied for a stomatitis-mitigating effect.

8-1 Test material

A test substance and a control substance were collectively used as test materials.

8-1-1 Test substance
Designation: OPB
Formula: olanexidine gluconate . . . 0.10 w/v %
  Pluronic L-44 . . . 0.07 w/v %
  Pluronic P-123 . . . 1.0 w/v %
8-1-2 Control substance
Designation/abbreviated name: base/Base
Formula: Pluronic L-44 . . . 0.07 w/v %
  Pluronic P-123 . . . 1.0 w/v %

8-2 Animal Used

Male Slc: Syrian hamsters which were 6 weeks old upon receipt were used to conduct a test on 8 animals per group.

8-3 Testing Method
8-3-1 Anesthesia
(1) At Time of Radiation Irradiation

Somnopentyl® (manufactured by Kyoritsuseiyaku Corp.) was intraperitoneally administered at 40 mg/kg.

(2) At time of stomatitis evaluation and test material administration

Gas anesthesia [induction of anesthesia: 3.0 L/min of air with 3% isoflurane (manufactured by Mylan Seiyaku Ltd.), the concentration of continuous anesthesia was appropriately adjusted] was carried out.

8-3-2 Stomatitis Model Making
(1) Radiation irradiation

On Day 0, the cheek pouch was pulled out from each hamster under anesthesia using a swab. Feed and floor mat for laboratory animals accumulated in the cheek pouch were removed, and the cheek pouch was patted with a cotton pad saturated with saline. The body and the cheek pouch were both fixed onto a molded acrylic plate. A region other than the cheek pouch at an irradiation site was covered with lead, and the cheek pouch was irradiated with radiation (40 Gy) under conditions of [shelf board distance: 12.5 cm, tube voltage: 160 kV, tube current: 6.2 mA]. However, the irradiation was performed for one cheek pouch per individual, and four animals with the left cheek pouch irradiated and four animals with the right cheek pouch irradiated were assigned to each group.

(2) 5-FU administration

5-FU was intraperitoneally administered at 60 mg/kg to the hamsters a total of three times on Days 0, 5, and 10.

8-4-3 Test material administration

Each hamster was fixed in the supine position under anesthesia, and 1 mL of each test material was injected to one cheek pouch. Thirty seconds later, the test material was eliminated, and a redundant test material was drawn out of the cheek pouch using a sterile swab. This administration by the gargling manipulation was performed twice a day. The administration was not carried out after the disorder of stomatitis reached the peak.

8-4-4 Stomatitis Evaluation

A stomatitis grade was evaluated on the basis of Table 4 above.

8-4-5 Statistical Analysis

A mean and standard deviation were determined on the stomatitis grade of each group, and a graph was created. No assay was conducted because of exploratory analysis.

8-5 Results

The results are shown in FIG. 16. The maximum value of the stomatitis grade was 4.9 for the base group and 4.3 for the OPB group, and furthermore, the grade started to rise earlier in the base group. The OPB group was evidently cured earlier, though all the animals were not completely cured because ulcer in some individuals was not healed even on Day 40 due to the influence of large strength of the models.

Example 9

9. Efficacy Test in Rat Gingivitis Model

In this test, the therapeutic effect of 0.1% olanexidine gluconate on gingivitis was studied in rat gingivitis models.

9-1 Test Material

A test substance and a control substance were collectively used as test materials.

9-1-1 Test substance
Designation: OPB
Formula: olanexidine gluconate . . . 0.10 w/v %
  Pluronic L-44 . . . 0.07 w/v %
  Pluronic P-123 . . . 1.0 w/v %
9-1-2 Control substance
Designation/abbreviated name: base/Base
Formula: Pluronic L-44 . . . 0.07 w/v %
  Pluronic P-123 . . . 1.0 w/v %

9-2 Bacterium Used

In this test, *Porphyromonas gingivalis* (ATCC No: 33277, manufactured by Microbiologics, Inc.) was used, which is a bacterium causative of gingivitis.

9-3 Animal Used

Male Jcl: Wistar rats which were 5 weeks old upon receipt were used to conduct a test on 5 animals per group.

9-4 Testing Method 9-4-1 Preparation of Test Bacterium (the Whole Manipulation Except for Preservation was Performed in an Anaerobic Chamber)

[1] A stored vial containing bacterial pellets was taken out and placed in an anaerobic chamber.
[2] One bacterial pellet was taken out of the vial and transferred to a sterile tube.
[3] 0.5 mL of a prepared TSB medium was added thereto.
[4] The bacterial pellet was squashed with a sterile swab to prepare a suspended bacterial fluid.
[5] The suspended bacterial fluid was inoculated to a sheep blood agar medium for CDC anaerobes.
[6] Culture was performed for 3 to 4 days under anaerobic conditions (37° C.)
[7] A single colony was selected from among the formed colonies, and similarly inoculated again to a sheep blood agar medium for CDC anaerobes.
[8] After confirmation of proliferation of bacteria, 3 mL of a prepared TSB medium was added thereto, and the bacteria were suspended using a spreader to make a glycerol stock.
[9] The stock was cryopreserved.
[10] The stock was inoculated to a sheep blood agar medium for CDC anaerobes and cultured under anaerobic conditions.
[11] After confirmation of proliferation of bacteria, the bacteria were suspended in an appropriate amount of a prepared TSB medium. A portion of the suspension was taken out, and the turbidity was adjusted to McFarland 5 using McFarland Standard. The dilution ratio was calculated, and the concentration of the bacterial suspension was adjusted to $1\times10^{10}$ CFU/mL from the remaining suspension.
[12] The resultant was used as a test bacterial suspension.
9-4-2 Anesthesia
(1) At time of cotton sewing thread insertion and autopsy
An aqueous pentobarbital sodium solution was intraperitoneally administered at 40 mg/kg.
(2) Bacterial inoculation and test material administration
Gas anesthesia [induction of anesthesia: 1.0 L/min of air with 5% isoflurane (Mylan Seiyaku Ltd.), the concentration of continuous anesthesia was appropriately adjusted] was carried out.
9-4-3 Cotton sewing thread insertion
After anesthesia, each animal was fixed in the dorsal position to a dedicated table, and a cotton sewing thread was inserted to between the upper right first and second molars with the lower jaw lifted.
9-4-4 Bacterial Inoculation
After anesthesia, 0.2 mL of the test bacterial suspension was inoculated to the cotton sewing thread insertion site. This manipulation was carried out every 2 hours.
9-4-5 Test material administration
After anesthesia, 1 mL of each test material was administered to cleanse the oral cavity. This manipulation was performed twice a day.
9-4-6 Observation and examination
(1) General Status
The general status was observed once a day from the cotton sewing thread insertion day to the autopsy day.
(2) Body Weight Measurement
The body weight was measured a total of twice from the cotton sewing thread insertion day to the autopsy day.
(3) Autopsy
Each animal was sacrificed by blood-letting from the cut abdominal aorta under anesthesia, and autopsy was performed.
(4) Histopathological Examination
The excised upper jaw was fixed in a 10 v/v % neutral buffered formalin solution, degreased, and decalcified, and HE-stained specimens were then made. Inflammatory change was pathologically examined as to each specimen.
9-4-7 Statistical analysis
A mean and standard deviation were calculated on the body weight of each group. No assay was conducted.
9-5 Results
No abnormality was observed in the general status, and the body weight did not differ between the groups.
The pathological examination results are shown in FIG. 17. The micrographs of the HE-stained specimens are shown in FIG. 18.
In the OPB administration group, the stratified squamous epithelium of the gingiva was observed with infiltration of neutrophils in 8 out of 10 cases, intercellular edematization in 1 out of 10 cases, and ulcer in 1 out of 10 cases, all of which were very slight. The lamina propria of the gingiva was observed with infiltration of neutrophils in 8 out of 10 cases and bleeding in 1 out of 10 cases, all of which were very slight. On the other hand, in the base administration group, the stratified squamous epithelium of the gingiva was observed with infiltration of neutrophils which was very slight in 8 out of 10 cases and was slight in 2 out of 10 cases. The stratified squamous epithelium of the gingiva was observed with intercellular edematization in 2 out of 10 cases, hyperkeratosis in 2 out of 10 cases, acanthosis in 2 out of 10 cases and ulcer in 1 out of 10 cases, all of which were very slight. The lamina propria of the gingiva was observed with infiltration of neutrophils which was very slight in 6 out of 10 cases and was slight in 3 out of 10 cases. The lamina propria of the gingiva was observed with bleeding and edematization, both of which were very slight in 1 out of 10 cases.
9-6 Discussion
All of infiltration of neutrophils, intercellular edematization, hyperkeratosis and acanthosis in the stratified squamous epithelium of the gingiva, and infiltration of neutrophils and edematization in the lamina propria were changes associated with an inflammation, and were considered to occur due to procedures. All of these changes tended to be low in terms of both frequency and degree in the OPB administration group compared with the base administration group. Therefore, an inflammation-mitigating effect brought about by OPB administration was observed.

Example 10

10. Efficacy Test in Rat Pneumonia Model
In this test, the therapeutic effect of 0.1% olanexidine gluconate on pneumonia was studied in rat aspiration pneumonia models.
10-1 Test Material
A test substance and a control substance were collectively used as test materials.
10-1-1 Test Substance
Designation: OPB
Formula: olanexidine gluconate . . . 0.10 w/v %
 Pluronic L-44 . . . 0.07 w/v %
 Pluronic P-123 . . . 1.0 w/v %
10-1-2 Control substance
Designation/abbreviated name: base/Base
Formula: Pluronic L-44 . . . 0.07 w/v %
 Pluronic P-123 . . . 1.0 w/v %
10-2 Animal Used
Male Crl: CD (SD) rats which were 7 weeks old upon receipt were used to conduct a test.
10-3 Group Configuration
The body weight was measured in the morning on the intratracheal administration day, and the animals were assigned by stratified randomization to 4 groups (groups 1 to 4) shown in Table 6 below. Six animals excluded from the assignment were assigned by stratified randomization to 2 groups (groups 5 and 6) shown in Table 6 below, and used as individuals for saliva collection.

TABLE 6

| Group No. | Administered substance | Timing of BALF collection (elapsed time after intratracheal administration) | n |
|---|---|---|---|
| 1 | Saliva (collected from group 5) | 6 h | 6 |
| 2 | Saliva (collected from group 5) | 24 h | 6 |
| 3 | Saliva (collected from group 5) | 6 h | 6 |
| 4 | Saliva (collected from group 5) | 24 h | 6 |

Individual for BALF recovery

| Group No. | Oral cavity cleansing (test material) | n |
|---|---|---|
| 5 | OPB | 3 |
| 6 | Base | 3 |

Individual for saliva collection 10-4 Testing method
10-4-1 Anesthesia
(1) Cleansing of Oral Cavity and Saliva Collection Somnopentyl was intraperitoneally administered at 40 mg/kg.

(2) At Time of Intratracheal Administration and Bronchoalveolar Lavage Fluid (BALF) Collection Gas anesthesia [induction of anesthesia: 3.0 L/min of air with 3% isoflurane (Mylan Seiyaku Ltd.), the concentration of continuous anesthesia was appropriately adjusted] was carried out.

10-4-2 Cleansing of Oral Cavity

A sterile swab was impregnated with each test material, which was then embrocated in a sufficient amount to the oral cavity under anesthesia.

10-4-3 Saliva collection 0.1% pilocarpine hydrochloride (5 mg/kg) was intraperitoneally administered under anesthesia. Over-secreted saliva was recovered. The recovered saliva was added to a nutritive medium containing a neutralizing agent, and left standing. Then, centrifugation (r.t., 3000 rpm, 10 min) was performed, and sediments were suspended in the same amount of saline to prepare an intratracheal administration solution.

10-4-4 Intratracheal Administration

After saliva collection, a tube for administration was indwelled in the trachea under anesthesia using a pharyngoscope, and 0.1 mL of saliva or saline was administered thereto.

10-4-5 BALF Collection

A median incision was made under anesthesia 6 or 24 hours after intratracheal administration, and each animal was euthanized by blood-letting from the incision in the abdominal aorta. Then, the lung was exposed, and a catheter was inserted to the origin of the bronchus. Lavage was performed three times (infusion and recovery were repeated twice for each time) with 8 mL of a PBS solution containing 0.1% BSA and 0.05 mM EDTA-2Na (hereinafter, referred to as PBS) through the line, and a lavage fluid was collected (BALF). BALF was centrifuged (200 g, 4° C., 10 min), and the supernatant was separated into other preservation tubes and used for LDH concentration measurement and measurement of cytokines (ELISA). Sediments were suspended in 1 mL of PBS and used for hematological examination.

10-4-6 Handling of Animal for Saliva Collection

After the completion of intratracheal administration, each animal for saliva collection was euthanized by blood-letting under, excess anesthesia.

10-4-7 Cytokine (TNF-α and IL-6) Concentration Measurement

The measurement was performed according to protocols included in kits.

10-4-8 Hematological Examination

Hematological analysis was carried out on the suspended sediments using an automatic blood cell counter for multiple items.

10-4-9 Biochemical Examination

An LDH concentration in the collected BALF supernatant was measured using an automatic analysis apparatus 7180 (Hitachi High-Technologies Corp.).

10-4-10 Statistical Analysis

No assay was conducted because of exploratory analysis.

10-5 Results

The hematological examination and biochemical examination results are shown in FIG. 19.

There was no difference between both the groups in the hematological examination. The 24-hour value of IL-6 was lower by 2.5 times in the OPB group. The value of TNF-α was lower in the OPB group at both the time points.

These results suggested that inflammatory reaction in the lung due to aspiration of saliva is lower in dealing of the oral cavity with OPB.

Example 11

11. Study on Anti-Inflammatory Action of Olanexidine Using TLR Reporter Cell Line Examples 6 to 10 indicated that olanexidine has anti-inflammatory action on stomatitis, gingivitis, and pneumonia. It has been revealed that inflammations are associated with immune response mediated by Toll-like receptor 4 (TLR-4) and Toll-like receptor 2 (TLR-2), which are receptors recognizing LPS or LTA (ChemMedChem. 2016 January 19; 11 (2): 154-65; Biotechnol Adv. 2012 January-February; 30 (1): 251-60; and J Dent Res. 2016 July; 95 (7): 725-33).

Olanexidine has the possibility of suppressing an inflammation by antagonistic (antagonist-like) action on TLR-4 and TLR-2. Accordingly, in this test, in order to elucidate this, the antagonistic (antagonist-like) action of olanexidine on TLR-4 and TLR-2 was confirmed by reporter assay using human-derived cells stably expressing TLR-4, TLR-2, and reporter (SEAP) genes.

11-1 Test substance

Designation: 1.5% OPB
Formula: olanexidine gluconate . . . 1.5 w/v %

11-2 Cell

The cells described in Table 7 below were used.

TABLE 7

| Designation (abbreviated name) | Host cell | Expressed gene | Catalog No./supplier | Medium |
| --- | --- | --- | --- | --- |
| TLR4/MD-2/CD14 Reporter Cell Line (HEK-TLR4) | HEK293 (human embryonic kidney-derived) | human Toll-like receptor 4 (TLR4), human MD-2, human CD14, secreted alkaline phosphatase (SEAP) reporter gene under the transcriptional control of a NF-κB response element | NBP2-26503/Novus Biologicals, LLC | DMEM (4.5 g/L glucose) + 10% FBS + 4 mM L-glutamine + 1 mM sodium pyruvate + 100 unit/mL penicillin* + 100 µg/mL streptomycin* + 10 µg/mL blastcidin*† + 2 µg/mL puromycin*† + 200 µg/mL zeocin*† + 500 µg/mL G418*† |
| TLR2 Reporter Cell Line (HEK-TLR2) | HEK293 (human embryonic kidney-derived) | human Toll-like receptor 2 (TLR2), secreted alkaline phosphatase (SEAP) reporter gene under the transcriptional control of a NF-κB response element | NBP2-26274/Novus Biologicals, LLC | DMEM (4.5 g/L glucose) + 10% FBS + 4 mM L-glutamine + 1 mM sodium pyruvate + 100 unit/mL penicillin* + 100 µg/mL streptomycin* + 10 µg/mL blastcidin*† + 500 µg/mL G418*† |

*Added, if necessary
†Selection reagent 11-3 Testing method
11-3-1 Study on antagonistic (antagonist-like) action of olanexidine on TLR-4
Cell used: HEK293 cells expressing TLR4
Medium used
Preculture: DMEM+FBS (final concentration: 10%)+ penicillin (final concentration: 100 units/mL) streptomycin (final concentration: 100 μg/mL)
Sample administration and culture after administration: DMEM+FBS (final concentration: 5%)
Activity measurement: SEAP assay kit (manufactured by Novus Biologicals)
Protein quantification: BCA protein assay (manufactured by Funakoshi Co., Ltd.)
[1] Cells were adjusted to $1.0 \times 10^5$ cells/well/100 μL with DMEM containing 10% FBS, seeded to a 96-well plate (collagen-coated), and cultured for 40 hours (37° C., 5% $CO_2$).
[2] 1.5% OPB was diluted to the concentrations shown in Table 8 below using 5% FBS.

TABLE 8

| | OPB concentration (μg/mL) |
|---|---|
| Preparation concentration | 20, 10, 5, 2 |
| Final concentration | 10, 5, 2.5, 1 |

[3] LPS was prepared at 20 ng/mL (final concentration: 10 ng/mL) using 5% FBS.
[4] After removal of the medium, media were added to the cells in the order of 50 μL of the OPB medium and 50 μL of the LPS medium, followed by culture for 8 hours (37° C., 5% $CO_2$).
[5] After the culture, 50 μL of the supernatant was transferred to each well of another 96-well plate, and SEAP assay was conducted.
[6] 50 μL of 0.1% SDS-0.1 N NaOH was added to each well of the 96-well plate from which the remaining supernatant was removed, and frozen overnight (−20° C.). After thawing, BCA protein assay was conducted.
[7] The expression level of the SEAP reporter gene was calibrated with the protein concentration to calculate an inhibition rate at each OPB concentration.
11-3-2 Study on antagonistic (antagonist-like) action of olanexidine on TLR-2
Cell used: HEK293 cells expressing TLR2
Medium used
Preculture: DMEM+FBS (final concentration: 10%)+ penicillin (final concentration: 100 units/mL) streptomycin (final concentration: 100 μg/mL)
Sample administration and culture after administration: DMEM+FBS (final concentration: 1%)
Activity measurement: SEAP assay kit (manufactured by Novus Biologicals)
Protein quantification: BCA protein assay (manufactured by Funakoshi Co., Ltd.)
[1] Cells were adjusted to $1.0 \times 10^5$ cells/well/100 μL with DMEM containing 10% FBS, seeded to a 96-well plate (collagen-coated), and cultured for 36 hours (37° C., 5% $CO_2$).
[2] 1.5% OPB was diluted to the concentrations shown in Table 8 above using 1% FBS.
[3] LTA was prepared at 2 μg/mL (final concentration: 1 μg/mL) using 1% FBS.
[4] After removal of the medium, media were added to the cells in the order of 50 μL of the OPB medium and 50 μL of the LTA medium, followed by culture for 12 hours (37° C., 5% $CO_2$).
[5] After the culture, 50 μL of the supernatant was transferred to each well of another 96-well plate, and SEAP assay was conducted.
[6] 50 μL of 0.1% SDS-0.1 N NaOH was added to each well of the 96-well plate from which the remaining supernatant was removed, and frozen overnight (−20° C.). After thawing, BCA protein assay was conducted.
[7] The expression level of the SEAP reporter gene was calibrated with the protein concentration to calculate an inhibition rate at each OPB concentration.
11-4 Results
The results are shown in FIG. 20.
The inhibition rate of SEAP was enhanced with elevation in OPB concentration ($IC_{50}$: approximately 10 μg/mL), demonstrating that OPB exhibits antagonistic (antagonist-like) action on TLR4 and TLR2. These results suggested that OPB has anti-inflammatory action by inhibiting immune response mediated by TLR4 and TLR2.

Example 12

12. Study on anti-inflammatory action of olanexidine using mouse macrophage-like cell line RAW264.7
A mouse macrophage-like cell line RAW264.7, when irritated with LPS or LTA, starts immune response via a receptor recognizing it, to produce an inflammatory mediator NO. Accordingly, whether olanexidine would have anti-inflammatory action on an inflammation due to LPS irritation was confirmed by using NO production from RAW264.7 cells as an indicator.
12-1 Test substance
Designation: 1.5% OPB
Formula: olanexidine gluconate . . . 1.5 w/v %
12-2 Cell
The cells described in Table 9 below were used.

TABLE 9

| Designation | Animal species | Tissue | Catalog No./supplier | Medium |
|---|---|---|---|---|
| RAW 264.7 | Mouse, BALB/c | Leukemic monocyte | EC91062702-F0/DS Pharma Biomedical Co., Ltd. | DMEM + 10% FBS + 100 unit/mL penicillin* + 100 μg/mL streptomycin* |

*Added, if necessary 12-3 Testing method
12-3-1 Study on anti-inflammatory action of olanexidine on LPS irritation Cell used: RAW264.7
Medium used
Preculture: DMEM+FBS (final concentration: 10%)+penicillin (final concentration: 100 units/mL) streptomycin (final concentration: 100 µg/mL)
Sample administration and culture after administration: DMEM+FBS (final concentration: 5%)
Activity measurement: Nitrate/Nitrite Colorimetric Assay Kit (manufactured by Griess Reagents)
Protein quantification: not measured because the cells were difficult to stain and destabilized values.

[1] Cells were adjusted to $1.0 \times 10^5$ cells/well/100 µL with DMEM containing 10% FBS, seeded to a 96-well plate (uncoated), and cultured for 24 hours (37° C., 5% $CO_2$).
[2] 1.5% OPB was diluted to the concentrations shown in Table 8 above using 5% FBS.
[3] LPS was prepared at 200 ng/mL (final concentration: 100 ng/mL) using 5% FBS.
[4] After removal of the medium, media were added to the cells in the order of 50 µL of the OPB medium and 50 µL of the LPS medium, followed by culture for 8 hours (37° C., 5% $CO_2$).
[5] After the culture, 50 µL of the supernatant was transferred to each well of another 96-well plate, and Nitrate/Nitrite colorimetric assay was conducted.

12-3-2 Study on Anti-Inflammatory Action of Olanexidine on *E. coli* (LPS-Producing Bacterium) Irritation Cell used: RAW264.7
Medium used
Preculture: DMEM+FBS (final concentration: 10%)+penicillin (final concentration: 100 units/mL) streptomycin (final concentration: 100 µg/mL)
Sample administration and culture after administration: DMEM+FBS (final concentration: 1%)
Activity measurement: Nitrate/Nitrite Colorimetric Assay Kit (manufactured by Griess Reagents)
Protein quantification: not measured because the cells were difficult to stain and destabilized values.

[1] Cells were adjusted to $1.0 \times 10^5$ cells/well/100 µL with DMEM containing 10% FBS, seeded to a 96-well plate (uncoated), and cultured for 24 hours (37° C., 5% $CO_2$).
[2] 1.5% OPB was prepared at the concentrations shown in Table 8 above using 1% FBS.
[3] After removal of the medium, 50 µL of the OPB medium was added to the cells, which were then left standing at 37° C. under 5% $CO_2$.
[4] *E. coli* cultured overnight in MHB was prepared at McF 1 and diluted 300-fold with 5% DMEM. Further, ampicillin was added thereto so as to attain a final concentration of 50 µg/mL.
[5] The prepared bacterial culture medium was further added at 50 µL/well to the plate supplemented with the OPB medium, and cultured for 24 hours (37° C., 5% $CO_2$) with the plate hermetically sealed.
[6] After the culture, 50 µL of the supernatant was transferred to each well of another 96-well plate, and Nitrate/Nitrite colorimetric assay was conducted.

12-4 Results

The results are shown in FIG. 21.

NO production was decreased with elevation in OPB concentration, demonstrating that OPB exhibits NO production-inhibiting action ($IC_{50}$: approximately 10 µg/mL). These results suggested that OPB has anti-inflammatory action.

INDUSTRIAL APPLICABILITY

The present invention provides a composition for amelioration and/or prevention of an inflammation, which is applicable to a wide range of inflammatory diseases. Moreover, use of the composition of the present invention as a composition for amelioration and/or prevention of oral mucositis due to treatment of a cancer can prevent reduction in QOL, such as inhibition of a communication function, sleep disorder, pain, or dysphagia (decreased dietary intakes), in a patient who is receiving chemotherapy and/or radiotherapy, or disturbance of dose conformity of chemotherapy and/or radiotherapy. Therefore, the present invention has high industrial usefulness.

The invention claimed is:

1. A method for treating and/or preventing an inflammation, comprising administering a therapeutically effective amount of a composition for treatment and/or prevention of an inflammation, comprising olanexidine or a pharmacologically acceptable salt thereof to a patient in need of treatment and/or prevention of an inflammation, wherein the inflammation is selected from stomatitis, gingivitis, and pneumonia.

2. The method according to claim 1, wherein the olanexidine or the pharmacologically acceptable salt thereof is olanexidine gluconate.

3. The method according to claim 1, wherein the composition further comprises a poloxamer which is a block copolymer consisting of a chain of polyoxypropylene (POP) and two chains of polyoxyethylene (POE) flanking the POP.

4. The method according to claim 3, wherein the poloxamer is selected from polyoxyethylene (42) polyoxypropylene (67) glycol, polyoxyethylene (54) polyoxypropylene (39) glycol, and polyoxyethylene (196) polyoxypropylene (67) glycol.

5. The method according to claim 4, wherein the poloxamer is polyoxyethylene (42) polyoxypropylene (67) glycol.

6. The method according to claim 1, wherein a concentration of the olanexidine gluconate in the composition is 0.05 to 0.5% (W/V).

7. The method according to claim 3, wherein a concentration of the poloxamer in the composition is 0.1 to 5.0% (W/V).

8. The method according to claim 1, wherein the composition is in a form of a liquid or a gargle.

9. The method according to claim 2, wherein the composition further comprises a poloxamer which is a block copolymer consisting of a chain of polyoxypropylene (POP) and two chains of polyoxyethylene (POE) flanking the POP.

* * * * *